US006284258B1

(12) United States Patent
Rose et al.

(10) Patent No.: US 6,284,258 B1
(45) Date of Patent: Sep. 4, 2001

(54) LONG-ACTING, CHEMICAL-RESISTANT SKIN EMOLLIENTS, MOISTURIZERS, AND STRENGTHENERS

(75) Inventors: Seth D. Rose; Rosemarie F. Hartman, both of Tempe; Carmen Chow, Gilbert, all of AZ (US); Cathryn M. Rose; K. Daniel Rose, both of Healdsburg, CA (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

(21) Appl. No.: 09/151,360

(22) Filed: Sep. 10, 1998

Related U.S. Application Data

(60) Provisional application No. 60/067,943, filed on Dec. 8, 1997.

(51) Int. Cl.[7] .......................... A61K 7/00; A61K 31/235; C07C 327/00
(52) U.S. Cl. .......................... 424/401; 514/543; 514/549; 514/550; 514/675; 514/678; 514/844; 558/251; 558/252; 558/255; 558/257
(58) Field of Search .................................... 558/255, 250, 558/251, 252, 257; 424/401; 514/543, 549, 675, 550, 678, 844

(56) References Cited

U.S. PATENT DOCUMENTS

| 4,323,517 | * | 4/1982 | Opitz et al. . | |
| 4,545,982 | | 10/1985 | Takahashi | 424/62 |
| 4,668,666 | | 5/1987 | Allan et al. | 514/63 |

(List continued on next page.)

FOREIGN PATENT DOCUMENTS

| 0753341 | 1/1997 | (EP) . |
| 2269523 | 11/1975 | (FR) . |
| 9404128 | 3/1994 | (WO) . |
| 98/18447 | 5/1998 | (WO) . |

OTHER PUBLICATIONS

Chem. Abstracts 77: Abstract No. =123284 (1972). Enoyl Coenzyme A Hydratase (Crotonase). Enhancement of the Rate of Hydration of Crotonyl Pantetherene by Coenzyme A and Related Compounds. Waterson et al., J. Biol. Chem. 247 (16), 5252–5257.

Ogawa et al., "The Histochemical Distribution of Protein Bound Sulfhydryl Groups in Human Epidermis by the New Staining Method," *J. Histochem. Cytochem.*, vol. 27, No. 5, pp. 942–946 (1979).

Schleppnick et al., "Thiolesters. Reaction of Thiols and Acrylyl and Crotonyl Chlorides," *J. Org. Chemistry*, vol. 29, pp. 1910–1915 (1964).

Khandelwal et al., "Derivatives of Sorbic Acid–Thiol Adducts," *Food Chemistry*, vol. 37, pp. 159–169 (1990).

Goldsmith, *Biochemistry and Physiology of the Skin*, p. 364 (Oxford University Press, New York and Oxford, 1983).

(List continued on next page.)

*Primary Examiner*—Diana Dudash
*Assistant Examiner*—Alysia Berman
(74) *Attorney, Agent, or Firm*—Baker Botts L.L.P.

(57) ABSTRACT

The present invention relates to compounds that are two-part molecules, and compositions containing such compounds, in which one part is designed to become covalently bonded to the skin (bonding agent) and the other part (a characteristic use agent) is designed to impart some characteristic use, such as emolliency, moisturizing effect, anti-acne, anti-wrinkle, anti-pain, antimicrobial, antifungal, antiviral, anti-irritation, skin tanning and skin lightening effects, extended protection of the skin (e.g., from ultraviolet light, by incorporation of a sunscreen component; from toxic and/or irritating substances; from insects and skin parasites, by incorporation of insecticides and/or insect repellants; from free radicals or other agents, as in aging, by incorporation of antioxidants), or dyeing of hair, skin nails, wool or fuir. The covalently bonded part may also be useful to impart skin strengthening effect (e.g., from shear forces) or as wound healing agents.

3 Claims, 1 Drawing Sheet

U.S. PATENT DOCUMENTS

| | | | |
|---|---|---|---|
| 4,696,676 | 9/1987 | Wilson et al. | 44/75 |
| 4,791,217 | 12/1988 | Robert et al. | 560/55 |
| 4,937,370 | 6/1990 | Sabatelli | 560/45 |
| 4,976,953 | 12/1990 | Orr et al. | 424/47 |
| 4,985,459 | 1/1991 | Sunshine et al. | 514/561 |
| 4,999,186 | 3/1991 | Sabatelli et al. | 424/60 |
| 5,073,371 | 12/1991 | Turner et al. | 424/401 |
| 5,073,372 | 12/1991 | Turner et al. | 424/401 |
| 5,087,445 | 2/1992 | Haffey et al. | 424/59 |
| 5,106,622 | 4/1992 | Sherwood et al. | 424/195.1 |
| 5,279,834 | 1/1994 | Meybeck | 424/450 |
| 5,411,992 | 5/1995 | Eini et al. | 514/731 |
| 5,434,190 | 7/1995 | Steltenkamp | 514/629 |
| 5,472,698 | 12/1995 | Rawlings et al. | |
| 5,490,980 | 2/1996 | Richardson et al. | 424/94.6 |
| 5,536,500 | 7/1996 | Galey et al. | 424/401 |
| 5,552,158 | 9/1996 | Evans et al. | 424/450 |
| 5,602,259 | 2/1997 | Boo et al. | 549/313 |
| 5,607,980 | 3/1997 | McAtee et al. | 514/476 |
| 5,700,784 | 12/1997 | Shinojima et al. | 514/24 |
| 5,738,862 | 4/1998 | Abraham | 424/403 |
| 5,785,959 | 7/1998 | Wolf et al. | 424/64 |
| 5,877,204 | 3/1999 | Davison et al. | |

OTHER PUBLICATIONS

Hall, *The Aging of Connective Tissue*, pp. 40–42 and 79–80 (Academic Press, New York, 1976).

Imayama et al., "A Hypothetical Explanation for Aging of Skin—Chronologic Alteration of the Three–Dimensional Arrangement of Collagen & Elastic Fibers in Connective Tissue," *Am. J. Pathol.*, vol. 134, No. 5, p. 1019 (1989).

Idson, "Dry Skin—Moisturizing and Emolliency," *Cosm. & Toil.*, vol. 107, p. 69 (1992).

Loden et al., "Product Testing—Testing of Moisturizers," in *Bioengineering of the Skin: Water and the Stratum Corneum*, p. 275 (Elsner et al. eds, CRC Press, Boca Raton, FL, 1994).

Rothman, "Insensible Water Loss," *Physiology and Biochemistry of the Skin*, p. 233–239 (University of Chicago, 1954).

Blank et al., "The Diffusion of Water Across the Stratum Corneum As a Function of Its Water Content," *J. Invest. Dermatol.*, vol. 82, No. 2, pp. 188–194 (1984).

MacMillan et al., "Interaction of Carbonyl Compounds with Organometallic Azides. V. Sorboyl Chloride and Its Conversion to an α–Pyridone," *J. Org. Chem.*, vol. 38, No. 17, p. 2982 (1973).

Tieke, "Solid state polymerization of butadienes. Polymerization of long chain derivatives of sorbic and muconic acid," *Colloid Poly. Sci.*, vol. 263, pp. 965–972 (1985).

* cited by examiner

LONG-ACTING, CHEMICAL-RESISTANT SKIN EMOLLIENTS, MOISTURIZERS, AND STRENGTHENERS

This application claims benefit of provisional application No. 60/067,943, filed Dec. 8, 1997.

FIELD OF THE INVENTION

This invention relates to compounds that are two-part molecules in which one part is designed to become covalently bonded to skin (bonding agent) and the other part (a characteristic use agent) is designed to impart some characteristic use, such as emolliency, moisturizing effect, anti-acne, anti-wrinkle, anti-pain, antibacterial, antifungal, antiviral, anti-irritation, skin tanning and skin lightening effects, extended protection of the skin (e.g., from ultraviolet light, by incorporation of a sunscreen component; from toxic and/or irritating substances; from insects and skin parasites, by incorporation of insecticides and/or insect repellants; from free radicals or other agents, as in aging, by incorporation of antioxidants), or dyeing of hair, skin, nails, wool or fur. The covalently bonded part may also be useful to impart skin strengthening effect (e.g., from shearing forces) or as wound healing agents. The invention also relates to a method of attaching the characteristic use agent to a water insoluble substrate such as fibers that contain or have been modified to contain a chemical group that can covalently react with the bonding agent.

BACKGROUND OF THE INVENTION

The entire surface of the human body is covered by a layer of skin, which is considered to be the largest organ in the body. It serves as a barrier between the internal organism and the external environment, to prevent toxic materials from entering into the body and to retard excessive body water loss. In addition, it also plays a major role in temperature regulation, vitamin synthesis, excretion, sensory perception, and processing of antigenic substances.

The skin consists of three major layers of tissue. From inside out, the layers are the subcutaneous tissue, the dermis, and the epidermis.

The epidermis is the most superficial layer of the skin. It is divided into a living inner layer of viable cells (stratum Malpighii) and an outermost laminated sheet of dry anucleate flattened horny cells (stratum corneum or horny layer).

The lowermost cell layer of the epidermis (stratum basale or stratum germinativum) consists of the basal cells. Basal cells are continually moving up to the surface of the skin and undergo modification in a process called keratinization, and are eventually shed. The normal cell turnover time from the stratum basale to the skin surface and shedding is approximately twenty-eight days. The stratum spinosum lies immediately over the basal layer. This stratum consists of several layers of cells, and the shape of these spinous cells becomes progressively more flattened in a plane parallel to the surface of the skin as they move outward. Above the spinous cells is the stratum granulosum, which consists of one to three layers of cells. The granular layer is most highly developed in the regions where abundant keratin is produced. Keratins are fibrous and insoluble proteins which are largely responsible for the toughness of the protective outer covering of the skin. The next stratum is the stratum lucidum, which consists of cells that are on the way to becoming the flat, anucleate and dead cells that constitute the stratum corneum. The stratum corneum is formed and continuously replenished by the slow upward migration of cells from the germinative basal layer of the epidermis. The entire stratum corneum is replaced about every two weeks in mature adults.

The condition of dry and chapped skin, which afflicts everyone at some time, is visually characterized as a slight roughening and less flexibility in the feel of the skin surface. Among dermatologists, this condition is called xerosis, in which the skin loses its suppleness, forming cracks and fissures. Environmental factors play an important role in bringing about this condition. Decreased humidity contributes to water loss from the skin surface, dry and cold winds increase evaporation by convection, and low temperatures decrease stratum corneum extensibility. The increased use of synthetic detergents also helps to dehydrate the stratum corneum.

The physical appearance of the slin is solely governed by the state of the stratum corneum. It has been demonstrated that the prime factor responsible for dry skin is the lowered moisture content of the stratum corneum. The factors that influence the state of hydration of the stratum corneum can be classified into three general categories: the rate at which water reaches the stratum comeurn from layers beneath it; the rate at which water leaves the skin surface by evaporation; and the ability of the stratum corneum to hold moisture.

The stratum corneum receives water from the sweat glands and from the underlying tissues by diffusion. At the same time, it loses water to the environment by evaporation. Under normal conditions, the rate at which water diffuses from the underlying tissues to the skin surface is slow and uniform. Experiments indicate that the major barrier against water loss over most areas of the body is a very thin barrier at the base of the stratum comeum, which separates the stratum comeum from the easily available water of the underlying tissues and makes it dependent upon the surrounding environment for the moisture. As a result, at low relative humidity, when water tends to be lost from the surface at a more rapid rate, the stratum corneum will tend to dry out.

The softness and flexibility of the skin is determined by the moisture content of the stratum corneum. Contrary to older beliefs, the amount of oil in the stratum corneum is not the essential factor in controlling the physical appearance of the skin. Thus pieces of hardened stratum corneum immersed in various oils do not regain their flexibility, whereas immersion in water increases their flexibility. However, the removal of the surface lipids of the skin after organic solvent treatment also brings about the feeling of dryness. This phenomenon demonstrates the water-holding ability of the skin lipids.

Various kinds of lipids are located in the intercellular region of the stratum corneum, which are called the intercellular lipids or the stratum corneum lipids. Stratum comeum lipids are composed mainly of ceramides, free fatty acids, and cholesterol, with small proportions of triglycerides, sterol esters, and cholesterol sulfate. The sphingolipid content is reported to reveal a direct relationship with permeability to water, while the neutral lipids are also suggested to make a definite contribution to the water-retention properties of the stratum corneum. Lipid compositions of different cell populations in pig epidermis are disclosed by Goldsmith, ed., *Biochemistry and Physiology of the Skin*, Oxford University Press, New York and Oxford, 1983, 364.

Dermal components of humans and animals have received much attention in the hope of identifying markers of biologic aging. The dermis is composed mainly of highly stable fibers, predominantly collagen and about 5% elastin fibers.

Collagen has high tensile strength and prevents the skin from being torn by overstretching. Elastin is an elastic protein that maintains normal skin tension. It is the collagen-elastin fiber network that gives the skin its strength and elasticity. Hall (1976) *The Aging of Connective Tissue*, Academic Press, New York used "the rods and elastic band" model to demonstrate the network of the collagen bundles in human skin. The collagen bundles are loosely arranged in a rhomboid network with individual bundles lying at angles to one another. Intertwined amongst the collagen bundles lie single elastin fibers. The network of collagen bundles can be distorted by the application of a force in one direction, but it returns to its original form when the force is removed, in exactly the same fashion that a network of rigid rods will resume its shape if each crossing point is restricted by an elastic band.

Both the collagen bundles and the elastin fibers seem to undergo characteristic changes with time. Imayama and Braverman (1989) *Am. J. Pathol.* 134:1019 reported that there is a dynamic rearrangement of the collagen and elastic fibers during the growth period of rats. The collagen bundles uncoil, thicken and develop a lattice pattern of relatively straight bundles with age. As the collagen bundles straighten, however, they bend and dislocate the elastin fibers. During adulthood, elastin fibers become increasingly tortuous and impart a frayed or porous appearance to the skin surface. The elastin fibers become more stretched and therefore a decrease in their original elasticity results. These phenomena lead to the looseness, sagging and wrinkling of aged skin.

Skin care products can be used to prevent excessive water loss or to restore the high moisture content of the stratum corneum. There are two groups of cosmetic products available for the treatment of dry skin conditions, emollients and moisturizers.

Emollients, often termed skin conditioners, increase and maintain hydration by lubricating or occluding the skin surface. They reduce the evaporative loss of water from the outside of the skin and cause a buildup of water in the stratum corneum. Emollients include a very wide range of compounds. They are all water-insoluble materials. Petrolatum is the most efficient emollient for protecting dry skin. Lanolin (a fatty secretion from sheep's wool, which consists of a mixture of fatty acid esters of the sterols, lanosterol and agnosterol), fatty acids, fatty alcohols, triglyceride esters, wax esters, and esters of polyhydric alcohols are all common emollients. Idson (1992) *Cosm. & Toil.* 107: 69.

Moisturizers are composed of hygroscopic substances. They often contain humectants, substances that attract moisture to the skin, such as urea, glycerin, propylene glycol, sorbitol, pyrrolidone carboxylic acid (PCA), or sodium lactate, to impart or restore moisture to the stratum corneum. Loden et al. (1994) "Product Testing—Testing of Moisturizers" in *Bioengineering of the Skin: Water and the Stratum Corneum*, Elsner et al., eds., CRC Press, Boca Raton, Fla., 275.

In order to evaluate moisturizer efficacy, and the irritation and barrier destruction potentials of soaps and solvents, the term "transepidermal water loss" (TEWL) was introduced. It is used to indicate the amount of water vapor passing through the stratum corneum by passive diffusion. In other words, TEWL is a true reflection of stratum corneum barrier function for water only in the absence of sweat gland activity. Rothman, "Insensible Water Loss" in *Physiology and Biochemistry of the Skin*, University of Chicago, 1954, 233.

The mathematical principle governing the diffusion of water through stratum corneum is Fick's law. TEWL is calculated according to the following integrated form:

$$J_s = K_m D(c_s/\delta) \qquad \text{eqn. 1}$$

where $J_s$=steady state flux of water (g cm$^{-2}$s$^{-1}$);

$K_m$=partition coefficient;

D=diffusion coefficient of water (cm$^2$s$^{-1}$);

$\delta$=thickness of the membrane (cm);

$c_s$=concentration gradient of water across the stratum corneum (g cm$^{-3}$).

The water content of the innermost layer of the stratum corneum is in equilibrium with the adjacent moist granular layer, which is in turn in equilibrium with the drier environment surrounding the skin. Thus, there exists a concentration gradient of water within the stratum corneum that results in a continuous diffusion of water from within the body through the skin and into the environment. The wetter the surface layer, the smaller the concentration gradient and the smaller should be the TEWL.

Upon hydration, the stratum corneum thickness $\delta$ increases due to swelling of the tissue; the diffusivity D also increases with increasing water content. Thus, the net result of a change in stratum corneum hydration on TEWL is not always predictable. However, in healthy skin, D usually predominates and TEWL increases.

The introduction of the partition coefficient $K_m$ into equation 1 takes account of the fact that in the diffusion process the concentrations at the surfaces of the membrane are not necessarily equal to the concentrations in the external solutions. $K_m$ is defined as $K_m = c_m/c_s$, where $c_m$=concentration of H$_2$O in the membrane (g H$_2$O cm$^{-3}$ of wet tissue); and $c_s$=concentration of H$_2$O in the solution (g H$_2$O cm$^{-3}$ of solution). Blank et al. (1984) *J. Invest. Dermatol.* 188.

It is an objective of the present invention to provide a compound that is capable of conferring a long-lasting skin care benefit. Currently available skin care products do not offer the convenient, long-term effects of the present invention. It is a further object of the present invention to provide a long-lasting compound that can be used in treating and preventing a dry skin condition, strengthening skin, or providing protection against UV light, for example by inducing a nucleophilic addition reaction to occur between the skin and the agent that provides these emolliency, moisturizing, strengthening or UV-protective effects. As a result, the agent is covalently bonded to skin proteins. Because new cells are continually being produced from the stratum basale to be shed, eventually, from the surface the binding period may last for possibly weeks to maintain the hydration and strengthening of the skin. Periodic application of the agent affords a virtually continuous maintenance of the beneficial effects, as the modified proteins work their way to the surface and reside in all the upper layers.

SUMMARY OF INVENTION

The present invention provides compounds that comprise at least one bonding agent and at least one characteristic use agent. The bonding agent is a chemical moiety which is capable of covalently bonding to one or more proteins in skin. The characteristic use agent is a chemical moiety which is capable of providing a skin care benefit. Skin care benefit, as used herein, means a cosmetic effect imparted by a particular characteristic use agent, such as but not limited to, the ability to provide emolliency, moisturing effect, or skin protectant effect, etc.

In certain embodiments, the bonding agent is selected from the group consisting of a crotonyl thiol ester, a sorbyl thiol ester or any other suitable α, β-unsaturated ester or thiol ester, and mixtures thereof; and the characteristic use agent is selected from the group consisting of emollients and skin soothing agents, moisturizers, sunscreens, insecticides, antibacterial agents, fungicides, antiviral agents, skin lightening agents, anti-acne agents, artificial tanning agents, free-radical scavengers, antioxidants, and mixtures thereof.

In a further embodiment the characteristic use agent can be connected to the bonding agent by a labile or cleavable linkage, resulting in a slow or long-term release of the characteristic use agent into the skin.

Exemplary compounds include octadecyl S-sorbyl-3-mercaptopropionate (hereinafter "OSM"), octadecyl S-crotonyl-3-mercaptopropionate (hereinafter "OCM"), S-crotonyl-ω-mercapto[poly(ethylene glycol)](hereinafter "CPEG"), S,S'-dicrotonyl-α-thio-ω-mercapto[poly(ethylene glycol)](hereinafter "DCPEG"), S-sorbyl-ω-mercapto[poly(ethylene glycol)](hereinafter "SPEG"), and S,S'-disorbyl-α-thio-ω-mercapto[poly(ethylene glycol)](hereinafter "DSPEG"), S-crotonyl-2-mercaptoethyl 4-methoxycinnamate (hereinafter "CMC"), and S-sorbyl-2-mercaptoethyl 4-methoxycinnamate (hereinafter "SMC").

The present invention further provides compositions comprising the compounds of the present invention and a cosmetically acceptable carrier. The present invention also encompasses methods of conferring a skin care benefit by applying to mammalian skin the compounds and compositions containing compounds of the present invention.

In an alternate embodiment one or more characteristic use agents can be bound to fibers that contain, or have been modified to contain, a suitable nucleophilic group that can react with the bonding agent.

The present compounds and compositions impart long-lasting skin care benefits, e.g., suppleness, emolliency and moisturizing effects, to skin and hair. The bonding agent is capable of covalently bonding to proteins in skin, thereby maintaining the characteristic use agent effects for possibly weeks by preventing loss of the characteristic use agents (e.g., by washing). Thus, the compounds and compositions containing the compounds of the invention help skin to resist the irritating effects of substances that remove skin lipids, such as detergents and organic solvents, help to resist the drying effect that results from skin exposure to the environment, or provide long-term sunscreen protection, depending upon the particular characteristic use agent present in the compound.

DETAILED DESCRIPTION OF INVENTION

Figure 1:
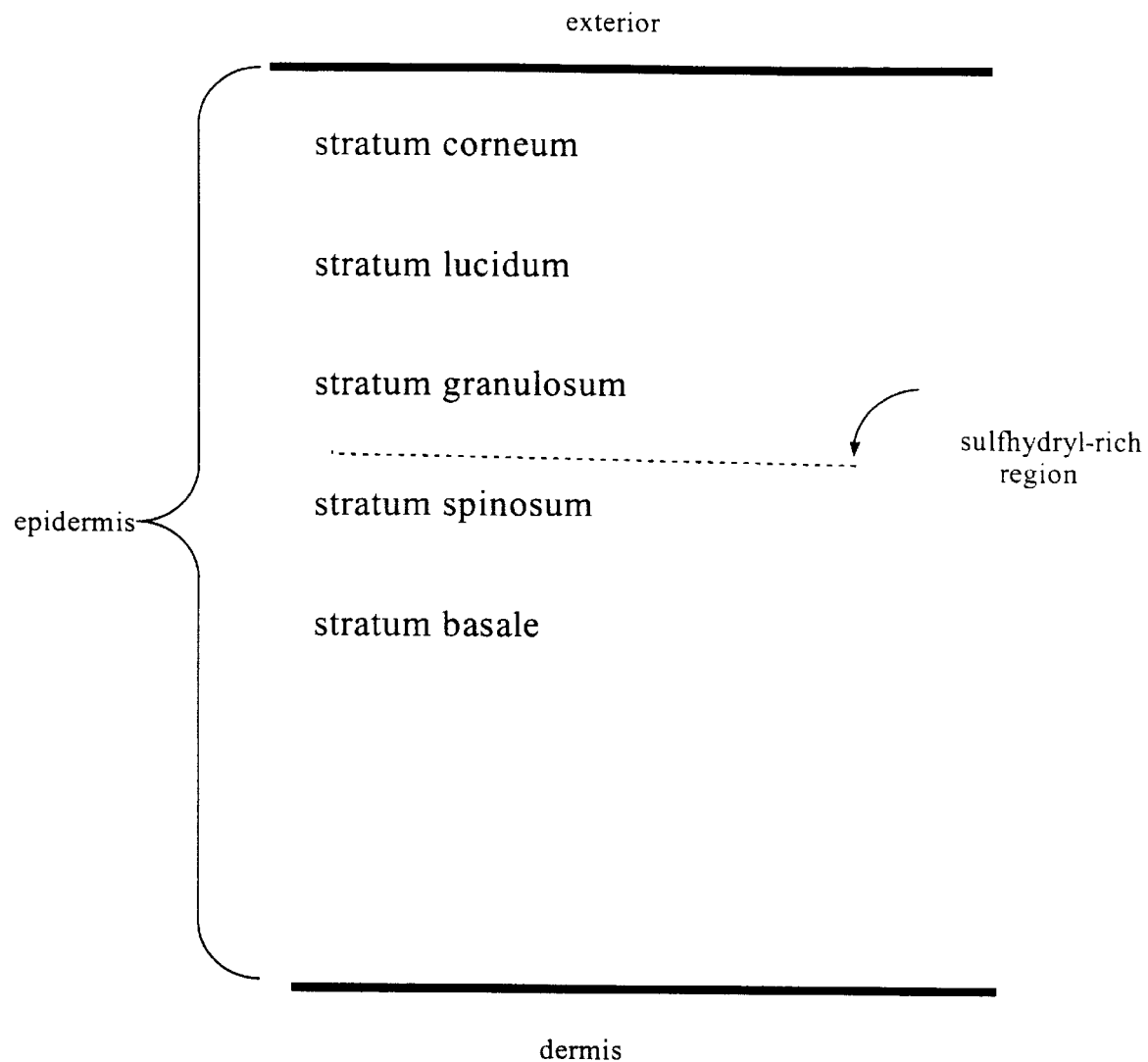
FIG. 1 is a diagrammatic illustration showing the anatomy of human skin including the sulfhydryl-rich region.

The present invention provides compounds that are two part molecules comprising a bonding agent and a characteristic use agent.

The compounds of the present invention have the generic formula

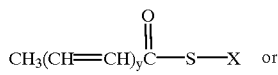

or

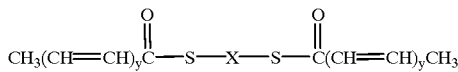

wherein each y is independently 1 or 2. The crotonyl thiol ester or sorbyl thiol ester moiety

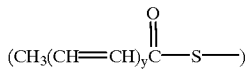

is the bonding agent and "X" is the characteristic use agent.

The characteristic use agent is selected from the group consisting of emollients and skin soothing agents, moisturizers, sunscreens, insecticides, antibacterial agents, fungicides, skin lightening agents, antiviral agents, anti-acne agents, artificial tanning agents, free-radical scavengers, antioxidants, and mixtures thereof. Suitable characteristic use agents, for use herein, can be found in the CTFA Cosmetic Ingredient Dictionary ($3^{rd}$ ed., 1982) and the CTFA Cosmetic Ingredient Handbook, (2nd ed., 1992), both published by The Cosmetic, Toiletry & Fragrance Association, Inc., which references are incorporated herein by reference in their entirety.

Emollients and skin soothing agents are known in the art and include, for example, oils, petrolatum, lanolin, fatty acids, fatty alcohols, triglyceride esters, wax esters, and esters of polyhydric alcohols. Suitable emollients and oils are disclosed by Idson (1992) Cosm. & Toil., 107:69 and U.S. Pat. No. 5,607,980, incorporated herein by reference. Skin soothing agents include bisabolol and non-steroidal, anti-inflammatory actives (NSAIDS) such as anesthetics. Examples of NSAIDS include propionic acid derivatives; acetic acid derivatives; fenamic acid derivatives biphenylcarboxylic acid derivatives; and oxicams. All of these NSAIDS are fully described in U.S. Pat. No. 4,985,459 to Sunshine et al., issued Jan. 15, 1991, incorporated by reference herein in its entirety. Examples of specific NSAIDS include acetyl salicylic acid, ibuprofen, naproxen, benoxaprofen, flurbioprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen and bucloxic acid. Also useful are the steroidal anti-inflammatory drugs including hydrocortisone and the like.

Examples of topical anesthetic drugs include benzocaine, lidocaine, buviacaine, chlorprocaine, dibucaine, etidocaine, mepivacaine, tetracaine, dyclonine, hexyclaine, procaine, cocaine, ketamine, pramoxine, phenol, and pharmaceutically acceptable salts thereof.

Moisturizers or humectants are known in the art and include, for example, materials selected from the group consisting of glycerol; guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches including sorbitol; sugars and starch derivatives (e.g., alkoxylated glucose); hyaluronic acid; pyrrolidone carboxylic acid; lactamide monoethanolamine; acetamide monoethanolamine; and mixtures thereof.

Also, useful are propoxylated glycerols as described in U.S. Pat. No. 4, 976,953, to Orr et al., issued Dec. 11, 1990, which is incorporated by reference herein in its entirety.

Suitable moisturizers are also disclosed by Loden et al. (1994), "Product Testing—Testing of Moisturizers," in *Bioengineering of the Skin: Water and the Stratum Corneum*, Elsner et al., eds, CRC Press, Boca Raton, Fla., 275.

Skin protecting agents are known in the art and are useful herein as a characteristic use agent and include sunscreens, insecticides, insect repellants, anti-acne additives, anti-wrinkle and anti-skin atrophy additives.

A wide variety of sunscreening agents are described in U.S. Pat. No. 5,087,445, to Haffey et al., issued Feb. 11, 1992; U.S. Pat. No. 5,073,372, to Tumer et al., issued Dec. 17, 1991; U.S. Pat. No. 5,073,371, to Turner et al., issued Dec. 17, 1991; and Segarin, et al., at Chapter VIII, pages 189 et seq., of *Cosmetic Science and Technology*, all of which are incorporated herein by reference in their entirety. Nonlimiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropy dibenzoylmethane, 3-benzylidene camphor, 3-(4-methylbenzylidene) camphor, anthanilates, ultrafine titanium dioxide, zinc oxide, silica and iron oxide and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening agents disclosed therein have, in a single molecule, two distinct chromophore moieties which exhibit different ultraviolet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens. Examples of these sunscreens include those selected from the group consisting of 4-N,N-(2-ethylhexyl)methylaminobenzoic acid ester of 2,4-dihydroxybenzophenone, 4-N,N-(2-ethylhexyl)-methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N(2-ethylhexyl)-methylaminobenzoic acid ester of 4-(2-hydroxyethoxy) dibenzoylmethane, and mixtures thereof.

Nonlimiting examples of anti wrinkle and anti-skin atrophy actives include retinoic acid and its derivatives (e.g., cis and trans); retinol, retinyl esters, salicylic acid and derivatives thereof; sulfur-containing D and L amino acids other than cysteine and their derivatives and salts, particularly the N-acetyl derivatives; alpha-hydroxy acids, e.g., glycolic acid, and lactic acid; phytic acid, lipoic acid, lysophosphatidic acid, and skin peel agents (e.g., phenol and the like).

Nonlimiting examples of insecticides, insect repellants and anti-arthropod agents include N,N-diethyl-m-toluamide, N-aryl and N-cycloalkyl neoalkonamide compounds as desecribed in U.S. Pat. No. 5,434,190 incorporated by reference herein, terpenoids, especially terpenoid alcohols and terpenoid-esters, aldehyde and ketones of texpenes as described in U.S. Pat. No. 5,411,992 incorporated by reference herein, oils of citronella, cedar and wintergreen as described in U.S. Pat. No. 5,106,622 incorporated by reference herein, 1-nonen-3-ol, and pyrethrum/pyrethoids as described in U.S. Pat. No. 4,668,666 incorporated by reference herein.

Antibacterial agents such as antibiotics and bactericides, and fungicides are known in the art and are useful herein as a characteristic use agent. Nonlimiting examples of useful antibacterial agents and fungicides include, β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chloretracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline, hydrochloride, oxytetracycline hydrochloride, clindamycin hydrochloride, ethambutol hydrochloride, metronidazole hydrochloride, pentamidine hydrochloride, gentamicin sulfate, kanamcyin sulfate, lineomycin hydrochloride, methacycline hydrochloride, methenamine hippurate, methenamine mendelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xyleneol, nystatin, tolnaftate and clotrimazole.

Skin lightening agents are known in the art and are useful herein as a characteristic use agent. Nonlimiting examples of useful skin lightening agents include glycosides of hydroxysalicylic acid and/or the glycosides of aliphatic esters of hydroxysalicylic acid as described in U.S. Pat. No. 5,700,784 incorporated by reference herein, hydroquinone, kojic acid or a derivative thereof, especially the salts or esters thereof as described in U.S. Pat. No. 5,279,834 incorporated by reference herein, 3-hydroxy-4(H)-pyran-4-one and its 3-acyl derivatives as described in U.S. Pat. No. 4,545,982 incorporated by reference herein, and 4-hydroxy-5-methyl-3[2H]-furanone.

Artificial tanning agents and accelerators are known in the art and are useful herein as a characteristic use agent. Nonlimiting examples of useful artificial tanning agents and accelerators include dihydroxyacetone, tyrosine, tyrosine esters such as ethyl tyrosinate, and phospho-DOPA.

Anti-Acne Actives are known in the art and are useful herein as a characteristic use agent. Nonlimiting examples of useful anti-acne actives include the keratolytics such as salicylic acid (o-hydroxy-benzoic acid), derivatives of salicylic acid such as 5-octanoyl salicylic acid, and resorcinol; retinoids such as retinoic acid and its derivatives (e.g., cis and trans); sulfur-containing D and L amino acids other than cysteine and their derivatives and salts, particularly their N-acetyl derivatives; lipoic acid; antibiotics and antimicrobials such as benzoyl peroxide, octopirox, tetracycline, 2,4,4'-trichloro-2'-hydroxydiphenyl ether, 3,4,4'-trichlorobanilide, azelaic acid and its derivatives, phenoxyethanol, phenoxypropanol, phenoxisopropanol, ethyl acetate, clindamycin and melclocycline; sebostats such as flavonoids; and bile salts such as scymnol sulfate and its derivatives, deoxycholate, and cholate.

Antiviral agents are also known in the art and useful herein as a characteristic use agent. Nonlimiting examples of antiviral agents include acyclovir, vidarabine, penciclovir, trifluridine, idoxuridine, podophyllotoxin and carbenoxolone.

Free radical scavengers and antioxidants are known in the art and are useful herein as a characteristic use agent. Nonlimiting examples of useful free-radical scavengers and antioxidants include butylated hydroxytoluene (BHT), butylated hydroxyanisole (BHA), tocopherols and their derivatives, ascorbic acid, its salts, derivatives such as ascorbyl palmitate and their salts, retinol and related carotenoids, bioflavonoids such as hesperitin, naringen, rutin, and quercetin, indole-3-carbinol, pycnogenol, melatonin, sulforaphane, pregnenolone, lipoic acid, amide and derivatives, 4-hydroxy-5-methyl-3[2H]-furanone, ferruginol type compounds as described in U.S. Pat. No. 5,552,158 and esters of cinnamic acid as described in U.S. Pat. No. 5,536,500, Galey incorporated by reference herein.

The aforementioned characteristic use agents can bound to fibers and other insoluble substrates as described in pending U.S. patent application Ser. No. 08/740,280 which either contain, or have been modified to contain, a nucleophilic group which can react with the bonding agent.

The compounds of the present invention may be synthesized by application of known organic chemical synthetic methods. Exemplary compounds include the following:

OSM

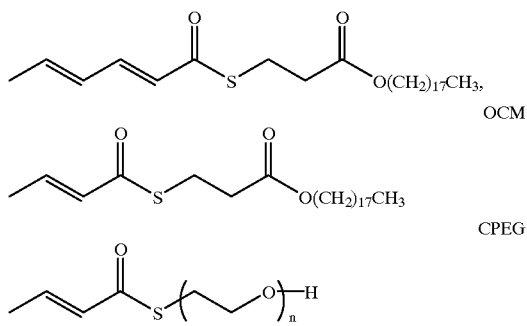

OCM

CPEG wherein n is primarily 8 to 9;

DCPEG

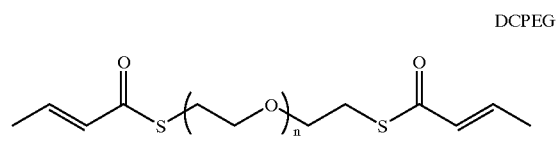

wherein n is primarily 7 to 8;

SPEG

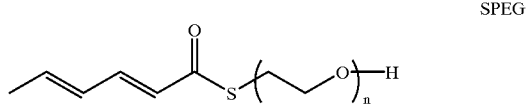

wherein n is primarily 8 to 9;

DSPEG

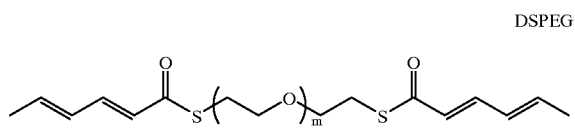

wherein m is primarily 7 to 8;

CMC

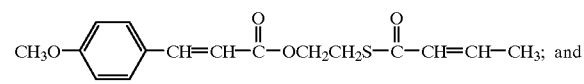

SMC

The compounds of the present invention covalently bond to skin by a reaction of the bonding agent of the present compounds with a nucleophilic group ($Nu^-$) of a skin protein without requiring an enzyme to catalyze the reaction. As used herein, the designation $Nu^-$ refers to nucleophilic groups contained in the skin including but not limited to sulfhydryl groups of cysteine residues, both in the neutral (—SH) and ionized forms (—$S^-$), including cysteine residues formed in situ by reduction of skin cystine residues, the —$NH_2$ of lysine residues and the N-terminus of proteins, the imidazole side chain of histidine residues, and the hydroxyl group of tyrosine residues, both in the neutral (—OH) and ionized (—$O^-$) forms.

The skin is rich in these nucleophilic groups. Free —SH residues of proteins are concentrated in the cell membrane or intracellular spaces in the junctional zone of living keratinocytes and the dead horny layer of human epidermis. The stratum spinosum—stratum granulosum boundary is rich in the neutral (—SH) and ionized (—$S^-$) forms of sulfhydryl groups of cysteine, shown diagramatically in FIG. 1. In the horny layer, the distribution of —SH groups is moderately high in the mid-stratum corneum, and then decrease gradually on the way up to the surface of the skin. Ogawa et al. (1979) J. Histochem. Cytochem. 27:942.

The reactivities of the compounds of the present invention are optimal in that the compounds are not so reactive as to induce skin irritation, nor damage essential biomolecules, nor produce harmful byproducts, whereas the compounds have sufficient reactivity to undergo reaction with skin nucleophiles (e.g. —$S^-$) under relatively mild conditions. The invention employs a novel kind of reaction, namely the conjugate addition reaction, in which nucleophiles attack a C═C that is conjugated to a thiol ester functional group. The addition reaction does not produce any by-products, as would have been generated by a nucleophilic substitution reaction (e.g., $Nu^- + R-X \rightarrow Nu-R + X^-$, where $X^-$ is a potentially undesirable by-product). The other novel aspect of the present compounds is the use of a thiol ester group, because it enhances the reactivity of the C═C that it is conjugated to more than an ordinary ester group does. Thus, for example, the α, β, γ, δ-unsaturated thiol ester group of OSM [C—C═C—C═C—C(═O)—S—R] and the α, β-unsaturated thiol ester groups of OCM, CPEG and CMC [C—C═C—C(═O)—S—R] are novel groups that are ideally suited for the desired reaction with skin nucleophiles.

To enhance the reaction between the present compounds and skin nucleophiles, a base, such as bicarbonate or triethanolamine, may be used in combination with the present compounds to convert the less nucleophilic —SH groups into the more nucleophilic —$S^-$ groups. The base converts some weak nucleophiles into strong nucleophiles (e.g., —SH into —$S^-$, tyrosine's —OH into —$O^-$, and reveals —$NH_2$ from the nonnucleophilic —$NH_3^+$ form).

Exemplary compounds of the present invention include OSM, OCM, CPEG, DCPEG, SPEG, DSPEG, CMC and SMC. The compound OSM consists of a two-part molecule. One part is designed to impart emolliency/moisturizing effects to skin, whereas the other part is designed to become covalently bonded to skin. An illustrative method of synthesizing OSM is provided at Example 1 hereinbelow. The part of the molecule designed to react with skin can do so with two different skin protein molecules or different regions of the same molecule, thereby crosslinking skin and adding to the skin's strength, and thus providing an important benefit for elderly individuals, who often have fragile, easily torn skin.

The covalent bonding of OSM to skin is based upon the nucleophilic attack of Nu⁻ groups in skin. A representative chemical reaction is as follows:

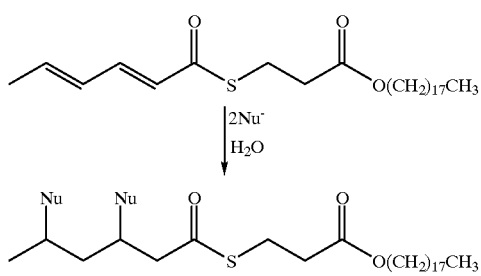

in which Nu⁻ in the chemical equation is as defined hereinabove. This chemical reaction describes one of the ways covalent attachment of OSM to skin can occur in water, although other solvents and other modes of covalent attachment are possible.

As a model for skin-bound sulfhydryl groups (—SH) of cysteine residues in skin proteins, the compound N-acetylcysteamine was allowed to react with OSM in the presence of a catalytic amount of the base 1,5-diazabicyclo[4.3.0]non-5-ene (DBN) in chloroform solution. The addition of N-acetylcysteamine to OSM, in a manner that is expected to parallel the addition of skin-bound nucleophiles (e.g., cysteine residues in skin proteins) to OSM, showed that covalent bond formation occurred, giving the compound shown below, or a related adduct.

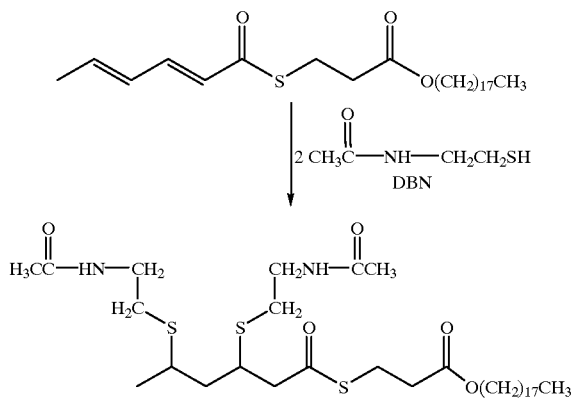

Covalent attachment also occurs between OSM and cysteine ethyl ester, another model for slin-bound cysteine residues in skin proteins, under similar conditions. The addition of cysteine ethyl ester to OSM in a manner that is expected to parallel the addition of skin-bound nucleophiles (e.g., cysteine residues of skin proteins) to OSM is thought to occur as shown below, or by a similar adduct formation path.

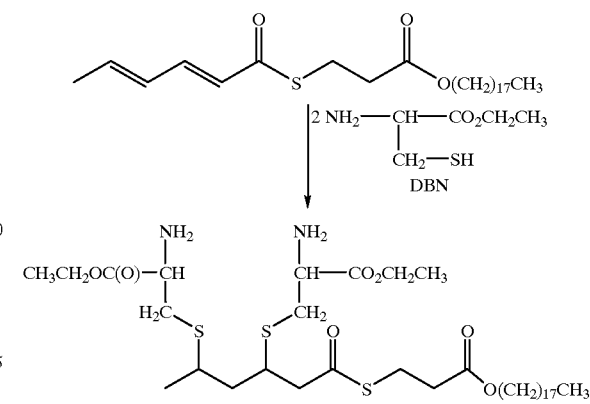

In the case of skin nucleophiles, the reaction shown below or an analogous adduct formation is expected to occur, in which a skin-bound sulfhydryl group (here illustrated with a cysteine sulfhydryl group) is the nucleophile illustrated to react with OSM.

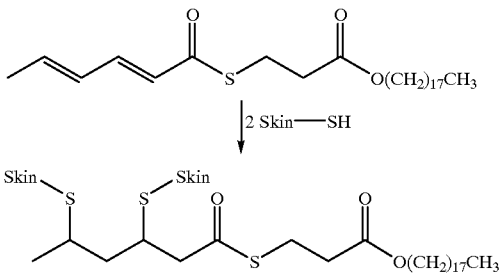

The compound OCM consists of a two-part molecule. One part is designed to impart emolliency/moisturizing effects to skin, whereas the other part is designed to become covalently bonded to slin. An illustrative method of synthesizing OCM is provided at Example 2 hereinbelow.

The covalent bonding of OCM to skin is based on the nucleophilic attack of Nu⁻ groups in skin. A representative chemical reaction is as follows:

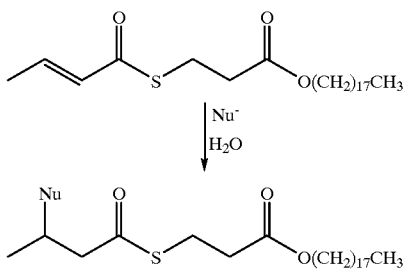

in which the Nu⁻ in the chemical equation is as defined hereinabove. This chemical reaction describes one of the ways covalent attachment of OCM to skin can occur in water, although other solvents and other modes of covalent attachment are possible.

As a model for skin-bound sulfhydryl groups (—SH) of cysteine residues in skin proteins, the compound N-acetylcysteamine was allowed to react with OCM in the presence of a catalytic amount of the base 1,5-diazabicyclo[4.3.0]non-5-ene (DBN) in chloroform solution. The addition of N-acetylcysteamine to OCM, in a manner that is expected to parallel the addition of skin-bound nucleophiles (e.g., cysteine residues in skin proteins) to OCM, showed that covalent bond formation occurred, giving the compound shown below, or a related adduct.

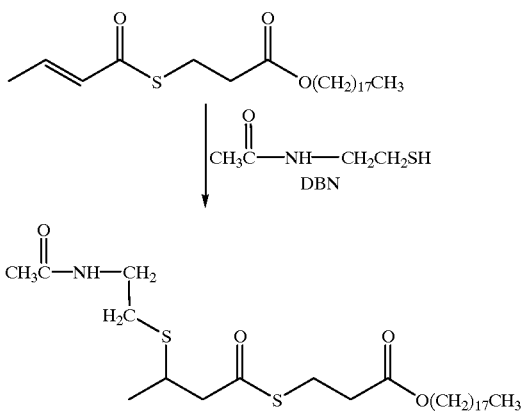

The reaction also occurred between OCM and cysteine ethyl ester, another model for skin-bound cysteine residues in skin proteins, under similar conditions. Addition of cysteine ethyl ester to OCM in a manner that is expected to parallel the addition of skin-bound nucleophiles (e.g., cysteine residues in the skin proteins) to OCM is thought to occur as shown below, or by a similar adduct formation path:

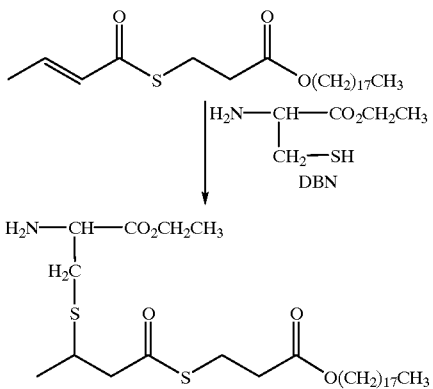

In the case of skin, the addition of skin-bound nucleophile is expected to occur as show n b elow or as an analogous adduct form ation, in which a skin-bound sulfhydryl group is the nucleophile illustrated to react with the OCM.

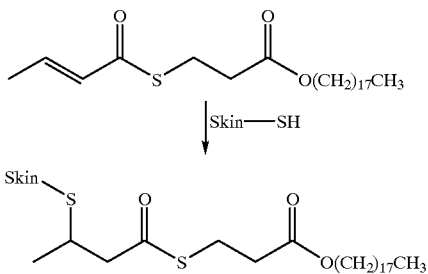

Exposure of skin to the environment or removal of skin lipids by detergents and organic solvents results in a skin-drying effect and irritation. The OSM and OCM molecules have lipid-like characteristics, principally due to the $(CH_2)_{17}CH_3$ group, that combat the drying effect and irritancy that the loss of skin lipids induces. Because of the covalent attachment of the lipid-like group to skin components such as proteins, which are not readily removed by detergents and organic solvents, the lipid-like portion resists removal by detergents and organic solvents, and imparts a protective effect to skin exposed to these agents.

To the extent that the binding of OSM and OCM to skin occurs at the deeper layers, e.g., the spinosum-granulosum boundary, over time these layers that contain the bound lipid-like group of OSM and OCM will evolve to the surface layers of the skin, through normal growth process of the skin. This may produce an even more beneficial protective effect on the skin, because the lipid-ike bound groups will be in an outer layer of the skin. Thus, the repeated application of OSM and OCM to skin might result, over a period of time, in virtually all layers of skin from relatively deep (e.g., spinosum-granulosum boundary) to the surface (e.g., stratum comeum) being chemically modified with the lipid-like chains of OSM or OCM.

Besides imparting chemical resistance and long-term emolliency/moisturizing effects to skin, the compounds of the invention may impart a skin-strengthening effect. This is a consequence of the potential of OSM to crosslink skin components, for example to link together different protein molecules in skin or different parts of the same protein molecule in skin. The potential beneficial effect of this is the strengthening effect that crosslinking has on polymers, such as skin proteins. Thus, for the elderly, who typically have easily torn and injured skin, the application of OSM might result in a strengthening of the skin and a decreased propensity for skin injury. As described above, this effect might increase over time with repeated application of the invention, as the lower layers of the skin bearing the crosslinked protein molecules evolve to the surface of the skin.

In addition to the uses described above, suitable sorbate thiol esters and crotonate thiol esters of a design apparent to those skilled in the art, having regard for this disclosure, have utility in the extended protection of skin, hair, nails, wool, and fur (e.g., from ultraviolet light, by incorporation of sunscreens into the thiol ester, from toxic and/or irritating substances, such as urushiol or urinary by-products; or from insects and parasites, by incorporation of insecticides and/or insect repellants), dyeing of hair, skin (e.g., tanning or marking, as with reflectant or colored substances), nails, wool, fur, and other substances with native nucleophilic groups or nucleophilic groups that can be added or revealed by suitable chemical and/or physical treatments.

The compounds CPEG, DCPEG, SPEG and DSPEG are two part molecules. One part is designed to become covalently bonded to skin, whereas the other part is designed to impart moisturizing effects or humectancy to the skin. Similar compounds that would accomplish substantially the same results are readily apparent to one skilled in the art, having regard for this disclosure. An illustrative method of synthesizing DCPEG is provided at Example 3 herein below.

As a model for skin bound sulihydryl groups (—SH) of cysteine residues in skin proteins, the compound N-acetylcysteamine was allowed to react with DCPEG in the presence of a catalytic amount of the base 1,5-diazabicyclo[4.3.0]non-5-ene (DBN) in chloroform solution. The addition of N-acetylcysteamine to DCPEG in a manner that is expected to parallel the addition of skin-bound nucleophiles (e.g., cysteine residues in skin proteins) to DCPEG, showed that covalent bond formation occurred, giving the compound shown below, or a related adduct.

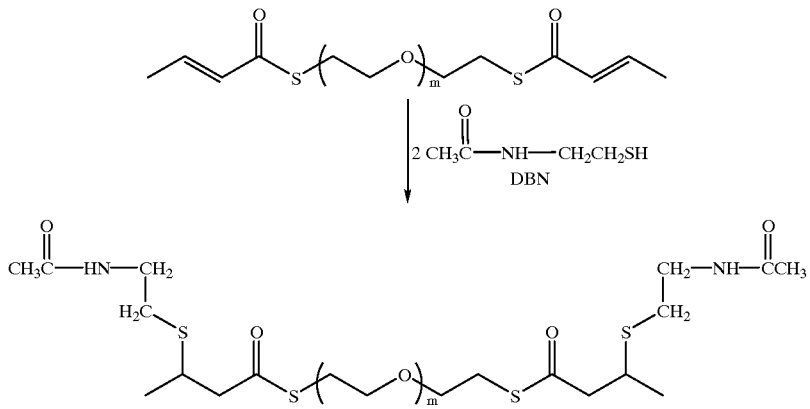

The covalent bonding of CPEG, DCPEG, SPEG, and DSPEG to skin is based upon the nucleophilic attack of Nu⁻ groups in skin. A representative chemical reaction using CPEG is as follows:

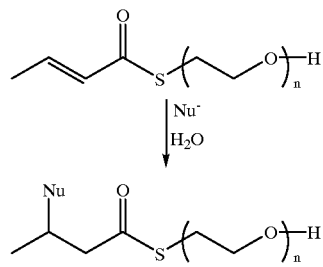

in which the Nu⁻ in the chemical equation is as defined hereinabove. This chemical reaction describes one of the ways covalent attachment of CPEG to skin can occur in water, although other solvents and other modes of covalent attachment are possible. A representative chemical reaction using DCPEG is as follows:

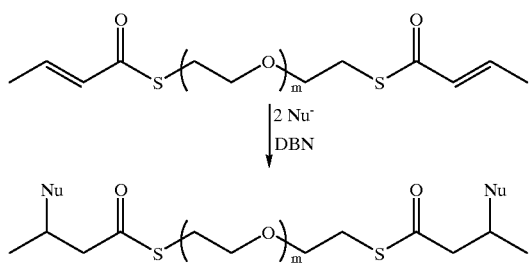

in which the Nu⁻ in the chemical equation is as defined hereinabove. This chemical reaction describes one of the ways covalent attachment of DCPEG to skin can occur in water, although other solvents and other modes of covalent attachment are possible. In this case, two skin-bound nucleophiles can become attached to one DCPEG molecule resulting in cross-linking of skin. This has the beneficial effect of strengthening skin, such as the fragile skin of the elderly.

A representative chemical reaction using SPEG is as follows:

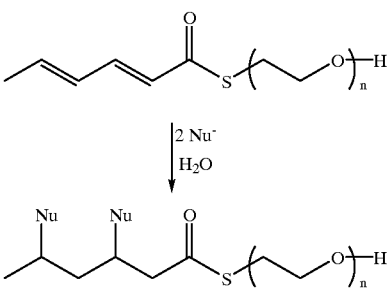

in which the Nu⁻ in the chemical equation is as defined hereinabove. This chemical reaction describes one of the ways covalent attachment of SPEG to skin can occur in water, although other solvents and other modes of covalent attachment are possible. Both of the reactive sites on SPEG need not necessarily react with skin nucleophiles for there to be a beneficial effect on skin.

A representative chemical reaction using DSPEG is as follows:

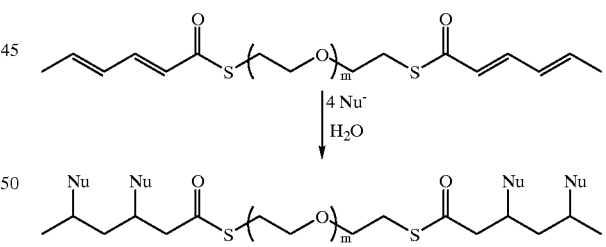

in which the Nu⁻ in the chemical equation is as defined hereinabove. This chemical reaction describes one of the ways covalent attachment of DSPEG to skin can occur in water, although other solvents and other modes of covalent attachment are possible. DSPEG can cross-link skin via the nucleophiles. However, not all four of the reactive sites of DSPEG need necessarily react with skin nucleophiles in order for there to be a beneficial effect on skin.

To enhance the reaction between CPEG, DCPEG, SPEG and DSPEG with skin nucleophiles, a base may be used in combination with CPEG, DCPEG, SPEG and DSPEG to convert the less nucleophilic —SH groups into the more nucleophilic —S⁻ groups. The base converts some weak nucleophiles into strong nucleophiles (e.g., —SH into —S⁻, tyrosine's —OH into —O⁻, and reveals —NH$_2$ from the nonnucleophilic —NH$_3^+$ form).

For example, in the case of skin nucleophiles, the reaction shown below or an analogous adduct formation is expected to occur, in which a skin-bound sulfhydryl group is the nucleophile illustrated to react with the CPEG:

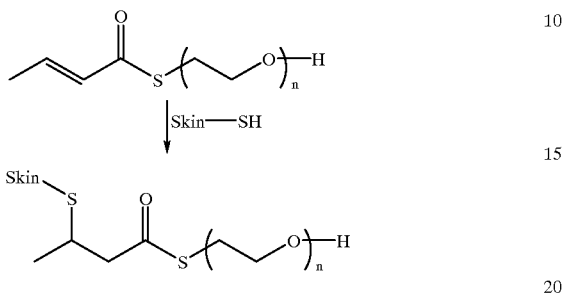

Loss of skin moisture through the action of detergents and organic solvents or exposure to the environment results in a skin drying effect (e.g., flaking) and irritation or aged appearance. The CPEG, DCPEG, SPEG and DSPEG molecules have a humectant or hydrophilic chain derived from poly(ethylene glycol) that resists the loss of skin moisture and assists the accumulation of moisture by the skin, i.e., rehydration of skin, thereby combating the irritancy and other effects that drying induces. The humectancy is presumably derived from the polyether chain (—CH$_2$ CH$_2$—O—) augmented by the terminal hydroxyl group in the cases of CPEG and SPEG. Because of the covalent attachment of the hydrophilic, moisture-holding group to the skin components such as proteins, which are not readily removed by detergents and organic solvents, a protective and restorative effect is imparted to skin exposed to these agents.

To the extent that the binding of one or more of CPEG, DCPEG, SPEG, and DSPEG to skin occurs at the deeper layers, e.g., the spinosum-granulosum boundary, over time these layers that contain one or more of the bound humectant group of CPEG, DCPEG, SPEG, and DSPEG will evolve to the surface layers of the skin though the normal growth processes of the skin. This may produce an even more beneficial protective effect on the skin, because the bound humectant groups will be in an outer layer of the skin. Thus, the repeated application of one or more of CPEG, DCPEG, SPEG, and DSPEG to skin might result, over a period of time, in virtually all layers of skin from relatively deep (e.g. spinosum-granulosum boundary) to the surface (e.g., stratum corneum) being chemically modified with the humectant part of CPEG, DCPEG, SPEG, and DSPEG.

The compounds CMC and SMC are two part molecules. One part is designed to become covalently bonded to skin, whereas the other part is designed to act as a sunscreen and impart protection to the skin against the harmful effects of exposure to ultraviolet light. Similar compounds that would accomplish substantially the same results are readily apparent to one skilled in the art, having regard for this disclosure.

French Patent No. 2,566,400, incorporated here by reference, describes the production of sulfur containing p-methoxycinnamates for use as sunscreens. The addition of a bonding agent as described by this invention forms CMC or SMC.

An illustrative method of synthesizing CMC is as follows.

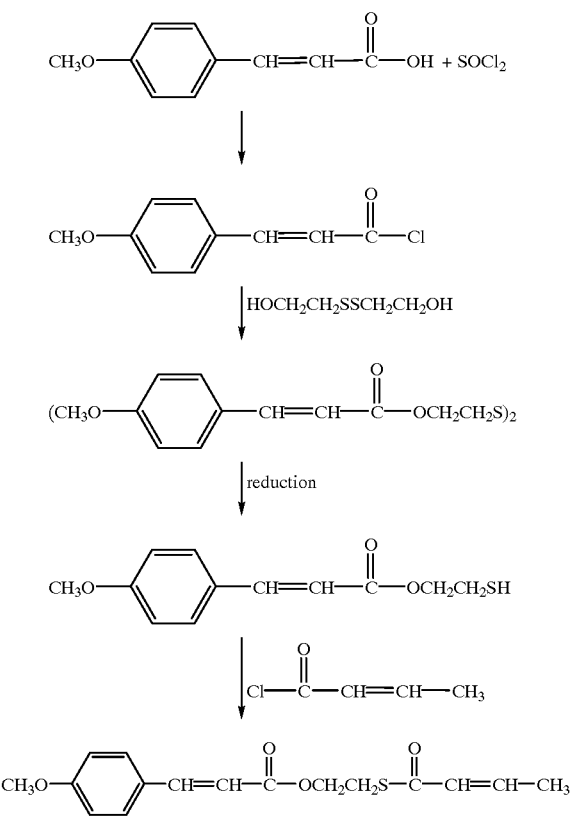

Similarly, an illustrative method of synthesizing SMC is as follows.

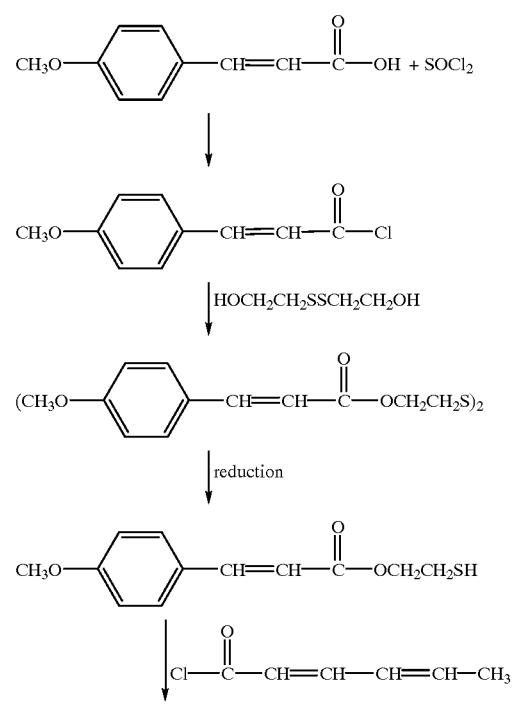

-continued

CH₃O—⟨⟩—CH=CH—C(=O)—OCH₂CH₂S—C(=O)—CH=CH—CH=CH—CH₃

The covalent bonding of CMC and SMC to skin is based on the nucleophilic attack of Nu⁻ groups in skin. A representative chemical reaction using CMC is as follows:

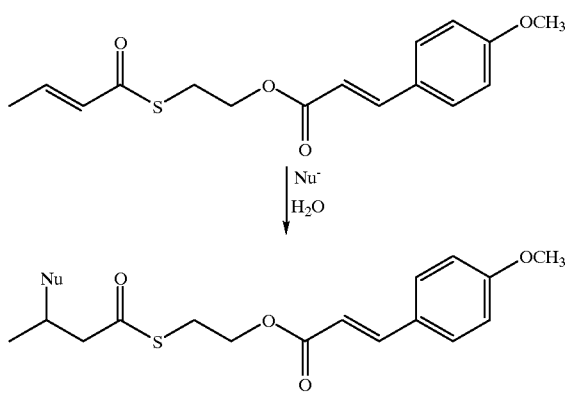

in which the Nu⁻ in the chemical equation is as defined hereinabove. This chemical reaction describes one of the ways covalent attachment of CMC to skin can occur in water, although other solvents and other modes of covalent attachment are possible.

A representative chemical reaction using SMC is as follows:

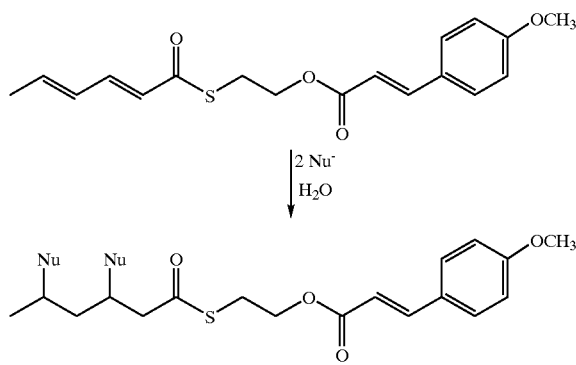

in which the Nu⁻ in the chemical equation is as defined hereinabove. This chemical reaction describes one of the ways covalent attachment of SMC to skin can occur in water, although other solvents and other modes of covalent attachment are possible. Both of the reactive sites of SMC need not necessarily react with the skin nucleophiles for there to be a beneficial effect on skin.

To enhance the reaction between CMC and SMC with skin nucleophiles, a base may be used in combination with CMC and SMC to convert the less nucleophilic —SH groups into the more nucleophilic —S⁻ groups. The base converts some weak nucleophiles into strong nucleophiles (e.g., —SH into —S⁻, tyrosine's —OH into —O⁻, and reveals —NH₂ from the nonnucleophilic —NH₃⁺ form).

For example, in the case of skin nucleophiles, the reaction shown below or an analogous adduct formation is expected to occur, in which a skin bound sulfhydryl group is the nucleophile illustrated to react with the CMC:

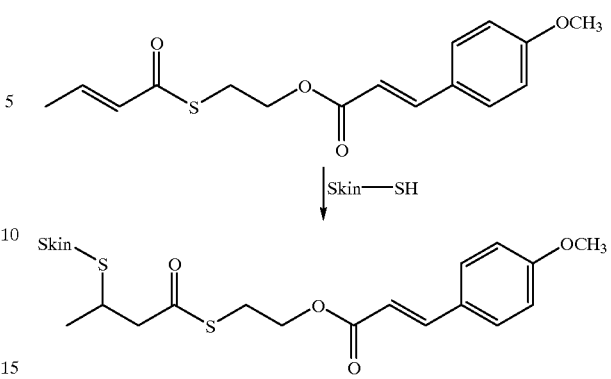

A similar reaction or formation of an analogous adduct would occur in the case of skin nucleophiles and SMC.

Exposure of the skin to ultraviolet light has been implicated as a possible factor in the induction of a number of harmful biological effects, such as skin aging and cancer. The CMC and SMC molecules have an ultraviolet light-absorbing group (4-methoxycinnamate) that imparts protection from effects of ultraviolet exposure. Because the ultraviolet light-absorbing group is covalently attached via the bonding agent to skin components, such as proteins which are not readily removed by detergents and organic solvents or exposure to the environment (e.g, water, wind, and abrasion), the ultraviolet light-absorbing portion resists removal by these agents.

To the extent that the binding of one or more of CMC and SMC to skin occurs at the deeper layers, e.g., the spinosum-granulosum boundary, over time these layers that contain one or more of the bound ultraviolet light-absorbing group of SMC and CMC will evolve to the surface layers of the skin though the normal growth processes of the skin. This may produce an even more beneficial protective effect on the skin, because the ultraviolet light absorbing groups will be in an outer layer of the skin. Thus, the repeated application of one or more of CMC and SMC to skin might result, over a period of time, in virtually all layers of skin from relatively deep (e.g. spinosum-granulosum boundary) to the surface (e.g., stratum corneum) being chemically modified with the ultraviolet light-absorbing sunscreen group of CMC and SMC.

From the foregoing it becomes readily apparent new and useful long-acting, chemical-resistant skin emollients, moisturizers, sunscreens and strengtheners and their preparations have been herein described and illustrated which fulfill all of the aforestated objectives. It is of course understood that such modifications, alterations and adaptations as will readily occur to the artisan confronted with this disclosure are intended within the scope of the invention.

The present invention further provides compositions comprising one or more compounds of the present invention and a cosmetically acceptable carrier which is compatible with the compound of the invention. Cosmetically acceptable carriers include water, alcohols, oils, and other carriers suitable for dissolving or dispersing the active ingredient. The compositions may further contain additional ingredients, such as fluidity promoters, colorants, perfumes, and the like. Suitable cosmetically acceptable carriers and additional ingredients, for use herein, can be found in the *CTFA Cosmetic Ingredient Dictionary* (3$^{rd}$ ed., 1982) and the *CTFA Cosmetic Ingredient Handbook*, (2nd ed., 1992), both published by The Cosmetic, Toiletry & Fragrance Association, Inc., which references are incorporated herein by reference in their entirety. The compositions are useful for application to the skin or hair as moisturizers, emollients, sunscreens or skin strengtheners, depending upon the particular characteristic use agent present in the compound of the invention.

Methods for the formulation of cosmetic compounds are well known to those of skill in the art. The compositions may take a form suitable for topical application, including for example a lotion, cream, gel, or solid, e.g. stick form, composition. The cosmetic compositions contain the compound of the invention in an amount that will be dependent upon the characteristic use agent portion of the two-part compound and the intended use of the composition. The compositions may contain the compound of the invention in an amount of about 0.1% to 35% by weight of the composition. For example, a compound of the present invention in which the characteristic use agent is a sunscreen agent will preferably be present in an amount of 0.1% to 15%, and more preferably 1% to 10% by weight of the composition. A compound of the present invention in which the characteristic use agent is an emollient will preferably be present in an amount of 1% to 35%, and more preferably 5% to 20% by weight of the composition. A compound of the present invention in which the characteristic use agent is a humectant will preferably be present in an amount of 1% to 20%, and more preferably 5 to 15% by weight of the composition. Formulations are described in Examples 4 and 5 herein below.

The following examples serve to further illustrate the present invention.

EXAMPLE 1

SYNTHESIS AND CHARACTERIZATION OF OSM AND n-OCTADECYL SORBATE (OS)

Material and Methods

All reagents used in the synthesis of the sorbate-based esters and thiol esters were purchased from Aldrich Chemical Co. or Lancaster Chemical Co., except octadecyl 3-mercaptopropionate was obtained from Hampshire Chemical Corp. Solvents were distilled prior to use. Evaporation of solvents was perfomed under reduced pressure on a Buchi rotary evaporator. THF refers to tetrahydrofuran, DBN to 1,5-diazabicyclo[4.3.0]non-5-ene and TEA to triethylamine. The THF was predried by refluxing over sodium and benzophenone until permanently purple and distilled under an $N_2$ atmosphere immediately before use. Analtech silica gel GF (0.25 mm) plates were used for thin-layer chromatography (TLC) and developed with a variety of solvents. A fluorescent indicator or an iodine chamber was employed for visualization of spots. Preparative silica gel thin layer chromatography plates (10 cm×20 cm, 1000 microns) were obtained from Analtech. Stationary phases used for gravity column chromatography were Baxter 70-230 mesh silica gel (VMR Scientific Co.). Tetramethylsilane and residual $CHCl_3$ (7.256 ppm) were used as internal references in all nuclear magnetic resonance measurements, which were determined with a Varian AM 300 Gemini spectrometer. Chemical shifts were recorded in ppm, and peak abbreviations for spin multiplicities are: s, singlet; d, doublet; t, triplet; dd, doublet of doublets; dt, doublet of triplets; m, multiplet; br, broad. Deuteriochloroform was used as an NMR solvent. Confirmation of structural data was given by the 2D COSY experiments. Melting points were measured on a Electrothermal Meltemp apparatus and are uncorrected.

Time-course NMR Spectral Study

A solution of octadecyl S-sorbyl-3-mercaptopropionate (10.9 mg, 0.024 mmol) in 0.3 mL of $CDCl_3$ was added to a solution of N-acetylcysteamine (5.2 μL, 0.048 mmol) and DBN (3.1 μL, 0.025 mmol) in 0.3 mL of $CDCl_3$. The mixture was immediately transferred to an NMR tube and the first spectrum was recorded at time=0. The reaction solution was allowed to stand at room temperature in the NMR tube for two days, and the course of the reaction was monitored by periodically recording the $^1H$ NMR spectrum. A total of ten $^1H$ NMR experiments were perfonned at time=0, 0.25, 0.5, 1, 1.5, 4.5, 12, 20.5, 26, and 39 hours.

Synthesis

Sorboyl chloride (1). To a 500-mL round-bottom flask containing 110 mL of cyclohexane, 3.85 g of sorbic acid was added at room temperature. The temperature was increased to 60° C. and 8.9 mL of thionyl chloride was added dropwise over a 1-hour period. The mixture was heated under reflux for 17 hours, after which the solvent and the unreacted thionyl chloride were evaporated in vacuo, and the mixture was concentrated to a brown residue: 4.05 g (90%) yield, $^1H$ NMR (300 MHz) δ 7.30 and 7.70 (total 1 H, m, HC=CCOCl), 5.8–6.6 (3 H, m, olefinic), and 1.9 (total 3 H, d, J=5 Hz, C$\underline{H}_3$CH=).

n-Octadecyl sorbate (OS). A solution of 0.9 g (6.9 mmol) of sorboyl chloride in 6 mL of THF was added slowly with stirring to a mixture of 1.87 g (6.9 mmol) of n-octadecanol in 10 mL of THF at 40° C. The resulting mixture was refluxed for 16 hours. The solvent was evaporated under reduced pressure and the crude product was purified by column chromatography on silica gel using chloroform as eluent. The appropriate fractions were combined and evaporated to dryness in vacuo to give a white solid product: 1.04 g (42%) yield. TLC ($CHCl_3$)$R_f$=0.75. $^1H$ NMR (300 MHz) δ 0.89 [3H, t, —(CH$_3$)$_{15}$C$\underline{H}_3$)],1.25 [30H, br m, —(CH$_3$)$_{15}$—], 1.62 [2H, t, —OCH$_2$C$\underline{H}_2$—], 1.86 [3H, d, C$\underline{H}_3$CH=], 4.14 [2H, t, —OCH$_2$—], 5.79 [1H, d, OCCH=], 6.19 [2H, m, CH$_3$C$\underline{H}$=C$\underline{H}$—], 7.22 [1H, m, CH$_3$CH=CH—C$\underline{H}$=].

Octadecyl S-sorbyl-3-mercaptopropionate (OSM). To a solution of 11.1 g (31.1 mmol) of octadecyl 3-mercaptopropionate dissolved in 30 mL of cyclohexane, at 45° C. was slowly added 4.05 g (31.0 mmol) of sorboyl chloride in 35 mL of cyclohexane. The resulting mixture was stirred and refluxed for 15 hours. The solvent was evaporated in vacuo, leaving a brown liquid. The resulting residue was applied to a column of silica gel and product was eluted with 10% ethyl acetate in hexanes solution. The appropriate fractions were combined and concentrated to give a white solid: 7.5 g (67%) yield. TLC (ethyl acetate/hexanes [10:90]) $R_f$=0.55. $^1H$ NMR (300 MH$_z$) δ 0.89 [3H, t, —(CH$_2$)$_{15}$-C$\underline{H}_3$], 1.24 [30H, broad m, —(CH$_2$)$_{15}$—], 1.61 [2H, t, —OCH$_2$C$\underline{H}_2$—], 1.94 [3H, d, C$\underline{H}_3$CH=], 2.63 [2H, t, —SCH$_2$C$\underline{H}_2$—], 3.20 [2H, t, —SC$\underline{H}_2$—], 4.08 [2H, t, —OC$\underline{H}_2$—], 6.02 [H, d, OCCH=]1, 6.20 [2H, m, CH$_3$C$\underline{H}$=C$\underline{H}$—], 7.20 [1H, m, OCCH=C$\underline{H}$—].

n-Octadecyl sorbate-N-acetyleysteamine monoadduct (2). To a solution of 109 mg (0.30 mmol) of n-octadecyl sorbate dissolved in 6 mL of cyclohexane/chloroform (50:50) was added 31.9 μL (0.30 mmol) of N-acetylcystearnine and 18 μL (0.15 mmol) of DBN. The mixture was heated at reflux for 15 hours, after which the solvent was evaporated in vacuo. The residue was placed onto a column of silica gel and product was eluted with 5% methanol in chloroform. The appropriate fractions were combined and concentrated to give a colorless oil (0.056 g, 39%). TLC (cyclohexane/chloroform [50:50])$R_f$=0.66, $^1H$ NMR (300 MHz) δ 0.89 [3H, t, C$\underline{H}_3$CH$_2$)$_{15}$—], 1.22 [30H, br m, CH$_3$(C$\underline{H}_2$)$_{15}$—], 1.31 [3H, d, C$\underline{H}_3$CH(S—)CH$_2$—], 1.61 [2H, t, —OCH$_2$C$\underline{H}_2$—], 2.00 [3H, s, acetyl], 2.44–2.72 [2H, two dd, —NHC$\underline{HH}$'—], 3.16 [2H, d, O=CCH$_2$—], 3.31–3.42 [3H, m, CH₃CH(SCH₂—)CH=], 4.08 [2H, t, —OCH₂—], 5.40 [1H, dd, C(3) olefinic], 5.55 [1H, dd, C(4) olefinic], 6.02 [1H, br s, amide proton].

Octadecyl S-sorbyl-3-mercaptopropionate-N-acetylcysteamine monoadducts (3 and 4). In a 50-mL round-bottom flask, 181 mg (0.40 mmol) of OSM was dissolved in 10 mL of chloroform, which was purged with nitrogen for 15 minutes prior to use. 30 μL (0.28 mmol) of N-acetylcysteamine and 39 μL (0.28 mmol) of triethylanine were added, and the solution was stirred under reflux in a nitrogen atmosphere for 2 hours. The solvent was evaporated and the mixture of monoadducts was isolated by preparative TLC with 3% methanol in chloroform. Rf=0.66. The isolated monoadducts mixture was spotted onto another preparative TLC plate, and the monoadducts were separated by repetitive developments with 3% methanol in chloroform.

¹H NMR (300 MHz) (monoadduct 3) δ 0.89 [3H, t, —(CH₂)₁₅CH₃], 1.30 [30H, br m, —(CH₂)₁₅—], 1.31 [3H, d, CH₃CH(S—)CH=], 1.61 (2H, t, —OCH₂CH₂—), 2.00 (3H, s, acetyl], 2.55 [1H, m, —NHCH₂CHH'—], 2.62 [2H, t, OC(O)CH₂], 2.65 [1H, m, —NHCH₂CHH'—], 3.12 [2H, t, O=CSCH₂—], 3.32 [3H, m, CH₃CH(SCH₂CH₂)CH=], 3.29 [2H, d, —SC(O)CH₂—], 4.10 [2H, t, —OCH₂(CH₂)₁₆—], 5.42–5.62 [2H, m, olefinic], 6.00 [1H, br s, amide proton]. COSY Correlations: δ 0.89/1.30,1.30/1.61, 1.31/3.44,1.61/4.10,2.55/2.65,2.62/3.12, 3.29/5.52,3.32/5.35, 5.35/5.52. ¹H NMR(300 MHz) (monoadduct 4) δ 0.89 [3H,t, —(CH₂)₁₅CH₃], 1.30 [30H, br m, —CH₂)₁₅—], 1.61 [2H, t, —OCH₂CH₂—], 1.71 (3H, d, CH₃CH=], 2.00 [3H, s, acetyl], 2.55 ]1H, m, —SCHH'CH₂NH—], 2.65 [1H, m, —SCHH'CH₂NH—], 2.61 [2H, t, —OC(O)CH₂—], 2.79 [2H d, —SC(O)CH₂—], 3.18 [2H, t, O=CSCH₂—], 3.40 [1H, dt, —NHCHH'—], 3.42 [1H, dt, —NHCHH'—], 3.63 [1H, m, CH₃CH=CHCH(S—)CH₂—], 4.08 [2H, t, —OCH₂(CH₂)₁₆—], 5.28 [1H, m, C(4) olefinic], 5.55 [1H, m, C(5) olefinic], 6.00 [1H, br s, amide proton]. COSY correlations: δ 0.89/1.30, 1/30/1.61, 1.61/4.10, 1.71/5.55, 2.55/2.65, 2.61/3.18, 2.55–2.65/3.40–3.42, 2.79/3.63, 3.40/3.42, 3.63/5.28, 5.28/5.55.

Reaction by-products Formation.

To a 25-mL round-bottom flask equipped with a drying tube, 45.2 mg (0.10 mmol) of OSM, 21.3 μL (0.20 mmol) of N-acetylcysteamine and 12.3 μL (0.10 mmol ) of DBN were dissolved in 5 mL of CHCl₃. The reaction mixture was allowed to stir at room temperature for 6 hours and was periodically monitored by TLC (ethyl acetate/hexanes [50:50]) for the disappearance of starting material. The solvent was evaporated under reduced pressure and the reaction crude mixture was purified by column chromatography on silica gel using 3% hexanes in methylene chloride solution. The isolated products were individually identified by NMR spectroscopy and their spectral data were summarized as follows:

Bis(octadecyl 3-mercaptopropionyl) disulfide (6). TLC (ethyl acetate/hexanes [50:50]) Rf=0.93. ¹H NMR (300 MHz) δ 0.89 [6H, t, methyl], 1.23 [60H, br m, —(CH₂)₁₅—], 1.61 [4H, t, —OCH₂CH₂—], 2.72 [4H, t, —SCH₂CH₂—], 2.94 [4H, t, —SCH₂—], 4.09 [4H, t, —OCH₂—].

N-Acetylcysteamino octadecyl 3-mercaptopropionyl disulfide (7). TLC (ethyl acetate/hexanes [50:50]) Rf=0.67, ¹H NMR (300 MHz) δ 0.89 [3H, t, methyl], 1.25 [30H, br m, —(CH₂)₁₅—], 1.62 [2H, t —OCH₂CH₂—], 2.00 [3H, s, acetyl], 2.74 [2H, t, —OC(O)CH₂—], 2.81 ]2H, t, —NHCH₂CH₂—], 2.94 [2H, t, —OC(O)CH₂CH₂—], 3.60 [2H, q, —NHCH₂—], 5.89 [1 H, br s, amide proton].

S-sorbyl 2-mercapto(N-acetyl)ethylamine (8). TLC (ethyl acetate/hexanes [50:50]) Rf=0.48, ¹H NMR (300 MHz) δ 1.87 [3H, d, methyl], 1.99 [3H, s, acetyl], 3.11 [2H, t, —SCH₂—], 3.44 [2H, t, —SCH₂CH₂—], 5.89 [1 H, br s, amide proton], 6.09 [1 H, d, OCCH=], 6.21 [2H, m, CH₃CH=CH—], 7.20 (1H, m, CH₃CH=].

As described above, OSM and OS were synthesized via the nucleophilic acyl substitution reaction of the sorboyl chloride with the corresponding thiol or alcohol, respectively.

The route for the preparation of these compounds is as follows.

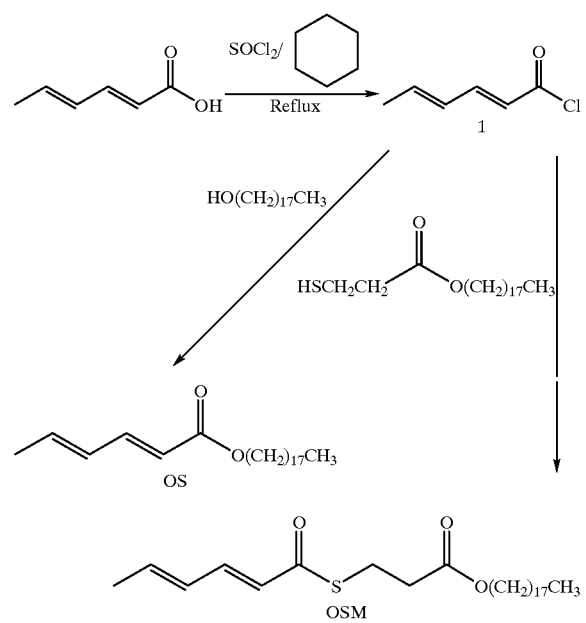

Sorboyl chloride was chosen based upon the fact that sorbic acid has been considered to be harmless and is included in the list of GRAS chemicals (generally regarded as safe). The preparation of sorboyl chloride starting material 1 was achieved by refluxing a cyclohexane solution of sorbic acid and thionyl chloride according to the procedure of MacMilan et al. (1 973) *J. Org Chem.*, 2982, except that the volatiles were removed by rotary evaporation instead of distillation. The yield of sorboyl chloride (90%) was the same as that reported by MacMilan et al. OS was prepared in 42% yield by treatment of 1 with 1 equiv of n-octanol in THF at reflux for 16 hours as described by Tieke (1995) *Colloid Poly. Sci.* 236:966. A similar procedure as that used in the preparation of OS was employed to prepare OSM; treatment of 1 with 1 equiv of octadecyl 3-mercaptopropionate in refluxing cyclohexane for 16 hours gave a 67% of OSM.

The study of the reaction between OSM and OS with the model skin protein, N-acetylcysteamine, demonstrated that both of the prospective emollient agents, OSM and OS, can be attached to the skin covalently via a nucleophilic addition as follows:

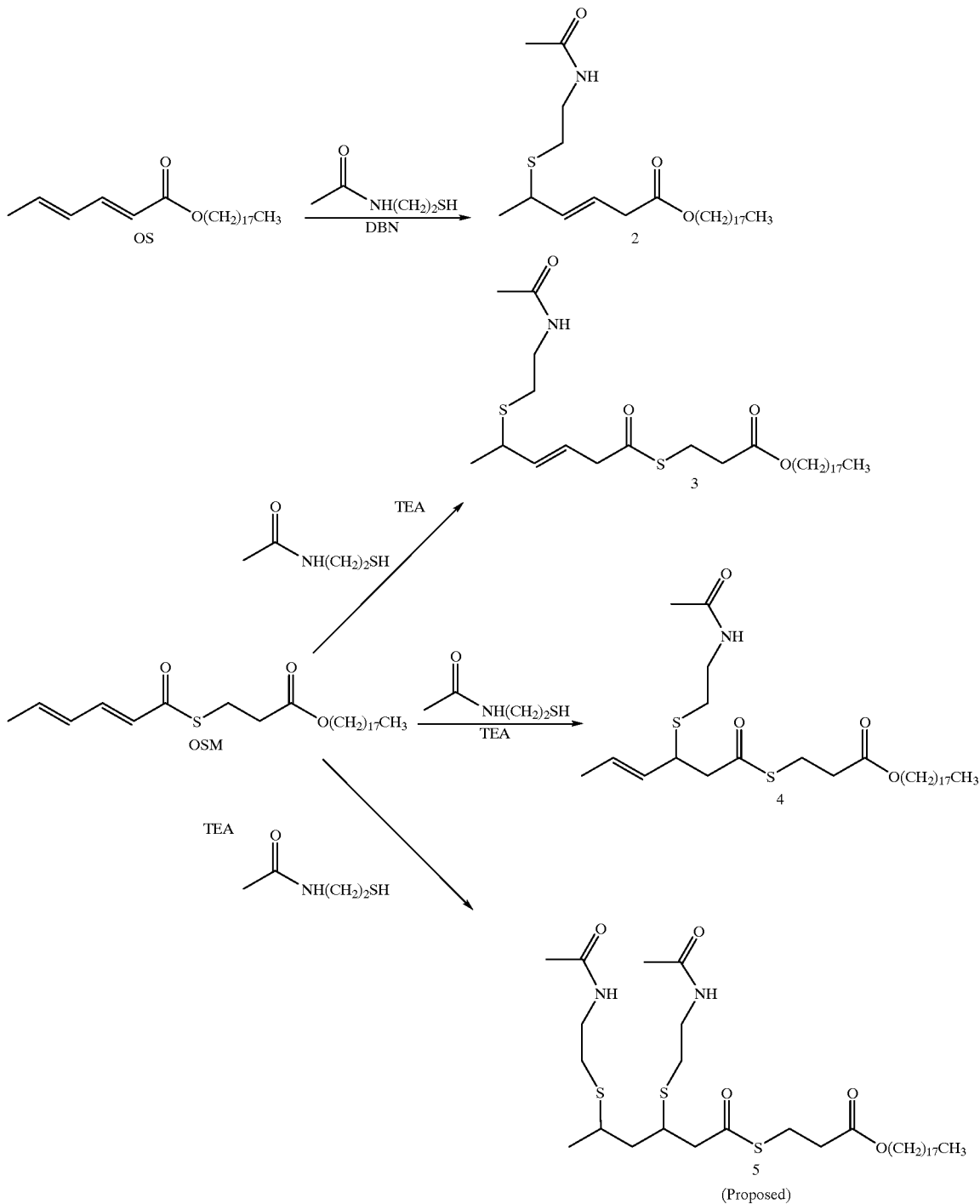

OS was allowed to react with 1 equiv of N-acetylcysteamine in the presence of 0.5 equiv of the base DBN in refluxing cyclohexane/chloroform mixture; the reaction gave the corresponding monoadduct 2 in 39% yield. Structural assignment of the monoadduct 2 was clearly made on the basis of its $^1$H NMR spectral data and 2D COSY correlations. The formation of the 2,5-addition product was confirmed.

The reaction of OSM with 0.7 equiv of N-acetylcysteamine in the presence of 0.7 equiv of triethylamine in chloroform at reflux, under an $N_2$ atmosphere, for 2 hours gave a mixture of two isomeric monoadducts, 3 and 4. The crude reaction mixture was concentrated to a small volume, which was subjected to column chromatography on silica gel for isolation. The method of column chromatography alone was insufficient to achieve a high level of purification; the two monoadducts eluted together. To separate the monoadducts 3 and 4, we employed the repetitive preparative TLC purification procedure. By analogy to the reaction of OS with N-acetylcysteamine, OSM would be expected to give monoadduct 3. In addition, monoadduct 4 was also obtained.

The $^1$H NMR spectra of both of the two monoadducts 3 and 4 exhibited the corresponding olefinic protons as a pair of multiplets at δ 5.6–5.4 and δ 5.6–5.2, respectively, and no signal assignable to olefinic protons at δ 6.2–6.0 and δ 7.2, attributable to the original dienyl portion of the sorbate group, —CH=CH—CH=CH—. The assignment of the olefinic proton signals was made on the basis of correlations in the 2D COSY spectra. These correlations indicated that the signals at δ 5.35 and δ 5.52 are due to the olefinic protons H-3 and H-4 of monoadduct 3; and the signals at δ 5.28 and δ 5.55 are due to the olefinic protons H-4 and H-5 of monoadduct 4. The upfield-shifted olefinic proton signal for C-4 in monoadduct 3 correlates with the multiplet signal at δ 3.32 for C-5, which in turn correlates with the methyl signal at δ 1.31 for C-6. The methyl doublet at δ 1.71 for C-6 correlates with the downfield-shifted olefinic signal at δ 5.55 for C-5 in monoadduct 4; and the aliphatic signals at δ 3.63 for C-3 correlates with the upfield-shifted olefinic signal at δ 5.28 for C4 as well as the doublet at δ 2.79 for C-2. The $^1$H NMR spectral results, together with the correlations in the 2D COSY spectra, demonstrated that both of the 2,5-addition product, 3, and the 2,3-addition product, 4, were formed in the reaction.

The time course of the reaction of OSM with 2 equiv of N-acetylcysteamine in the presence of 1 equiv of DBN in 0.6 mL of $CDCl_3$ was studied by recording $^1$H NMR spectra at various times for 39 hours. The signals of the olefinic protons due to the sorbate group of OSM (δ 6.2–6.0 and δ7.2) and that of the newly formed C=C bond of the monoadducts (δ 5.6–5.2) were monitored in particular. In the course of these experiments, it was observed that the signals at δ 6.2–6.0 and δ 7.2 disappeared, while those at δ 5.6–5.2 appeared over the first 1.5 hours of the reaction, which indicated the formation of the monoadducts. The olefinic protons signals of the monoadducts started to fade away gradually after 1.5 hours and became very weak by approximately 39 hours. These spectra may imply the formation of the diadduct.

Only one monoadduct 2 was isolated in the reaction of OS with N-acetylcysteamine, while two different monoadducts 3 and 4 were obtained in the reaction of N-acetylcysteamine with OSM. The varying reactivity of the C=C of the sorbate group of the different agents towards nucleophilic attack may account for the differences.

When reactions were carried out in the absence of an $N_2$/inert gas atmosphere, as an attempt to bind together the protein bound sulfhydryl groups with OSM, a range of side products were isolated by column chromatography, as shown below.

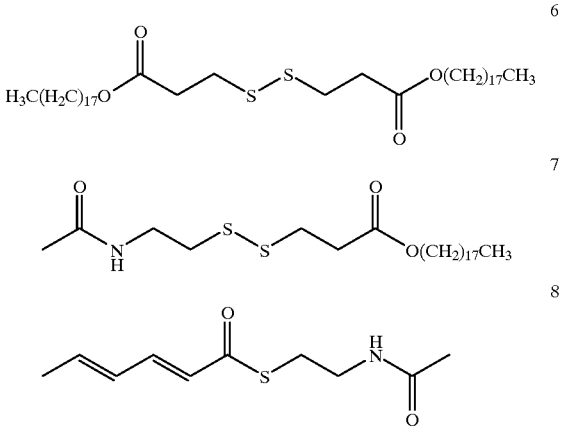

Two molecules of octadecyl-3-mercaptopropionate were oxidized to form a symmetrical Bis(octadecyl 3-mercaptopropionyl) disulfide 6. The unsymmetrical N-acetylcysteamino octadecyl 3-mercaptopropionyl disulfide 7 was made when one molecule of octadecyl 3-mercaptopropionate and one molecule of N-acetylcysteamine were oxidized and coupled. The by-product S-sorbyl 2-mercapto(N-acetyl)ethylamine 8 was also obtained in the reaction mixture. It was formed possibly from the attack of the carbonyl carbon of OSM followed by the displacement of the group octadecyl [3]-mercaptopropionate of OSM by the deprotonated N-acetylcysteamine thiolate anion. In contrast, the formation of the disulfide by-products was impossible in similar reactions with OS.

The proposed mechanism for the reactions is summarized below.

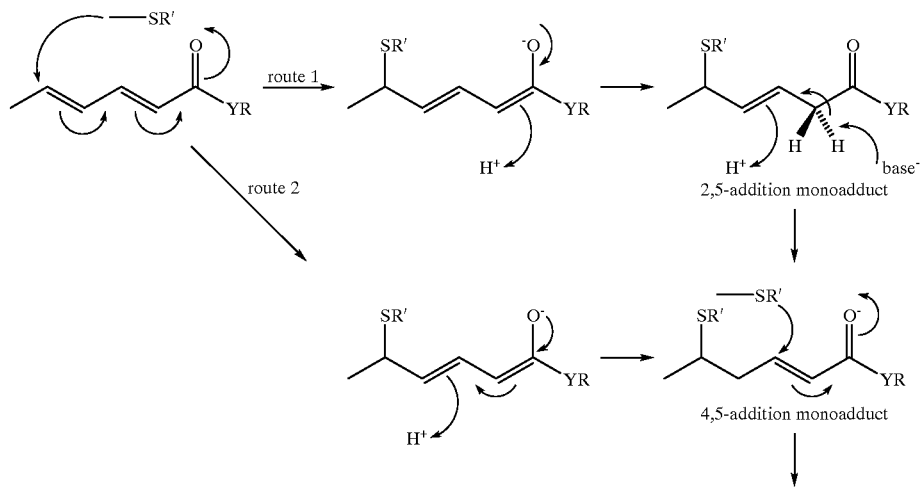

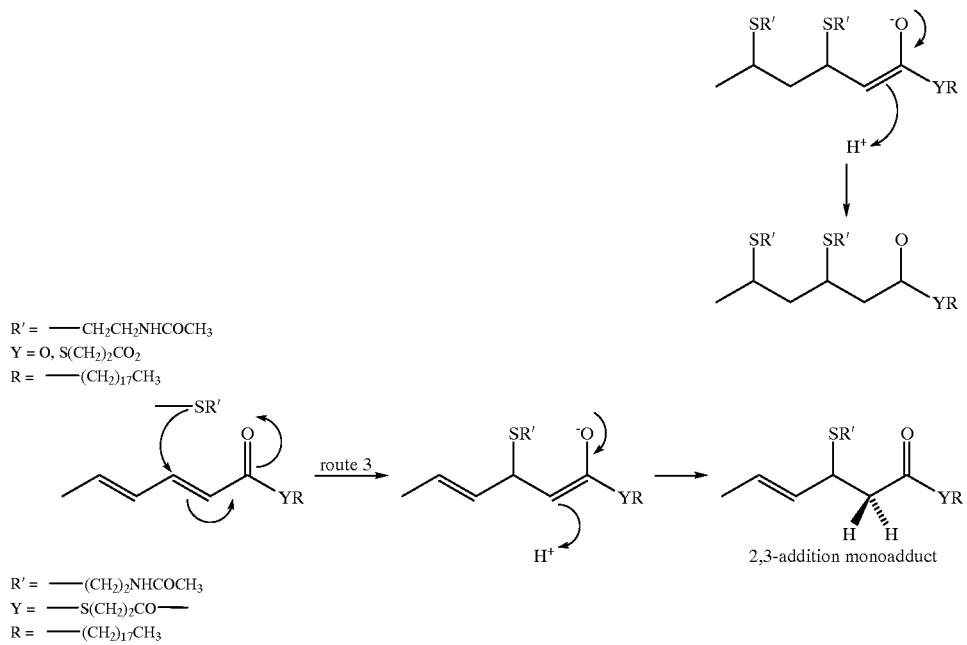

R' = —CH₂CH₂NHCOCH₃
Y = O, S(CH₂)₂CO₂
R = —(CH₂)₁₇CH₃

R' = —(CH₂)₂NHCOCH₃
Y = —S(CH₂)₂CO—
R = —(CH₂)₁₇CH₃

The nucleophilic attack by the thiolate anion (—RS—) at the δ-carbon atom of the sorbate group of OS or OSM results in an enolate intermediate, which protonates at the C-2 position to give a 2,5-addition monoadduct 2 or 3 (route 1). The 2,5-addition monoadduct has a double bond that is not conjugated to the carbonyl group and cannot undergo a further nucleophilic addition reaction to yield the desired diadduct compound. According to the results of the NMR spectral study of the time course of the reaction, the formation of the diadduct is of the greatest likelihood. In order to account for the observation, route 2 that leads to the formation of the 4,5-addition monoadduct suggests a better explanation for the possibility of the formation of the reaction diadduct. The resulting enolate intermediate protonates at the C-4 position and forms a monoadduct.that has a double bond that is conjugated to the carbonyl group and is capable of reacting further in a nucleophilic reaction. Subsequent attack by the thiol anion nucleophile at the 3-carbon of the 4,5-addition monoadduct would give the desired diadduct. Khandelwal (1990) Food Chemistry 37:159 suggested that, in the presence of a strong base, the 2,5-addition monoadduct may be converted to the 4,5-addition monoadduct by the abstraction of the α-proton and consequent protonation at the γ-carbon atom in the 2,5-addition monoadduct. However, the attempt to convert the isolated 2,5-addition monoadduct 3 to the 4,5-addition monoadduct in the presence of DBN was unsuccessful as determined by means of ¹H NMR analysis. Moreover, the 2,3-addition monoadduct 4 from the reaction between OSM and N-acetylcysteamine (route 3) that was isolated was believed to be unreactive to nucleophiles; thus, the formation of diadduct from 4 is not likely. The differences in the aforementioned results and the experimental observation of the time course ¹H NMR spectral study may be accounted for by differences in the experimental conditions.

The formation of the 4,5-addition monoadduct was not detected by ¹H NMR analysis in this reaction; Khandelwal et al. have reported similar results for reactions of other thiols with ethyl and methyl sorbates. The 4,5-addition monoadduct is believed to be the more stable reaction product as it contains a C=C bond that is conjugated to the carbonyl group. No evidence was obtained for the formation of this more stable monoadduct. One explanation is that the 4,5-addition monoadduct may have been formed during the course of the reaction, but it was immediately attacked by the second equiv of the thiol anion to form the desired diadduct.

The foregoing results demonstrate that both the selected thiol ester OSM and the ordinary ester OS react with N-acetylcysteamine, in the presence of a base, to form their corresponding 2,5-monoadducts, and in addition OSM formed a 2,3-addition monoadduct. These reactions demonstrate the capability of these prospective emollients to be attached to the sulfhydryl group of the protein residues of the skin, thus giving long-lasting emolliency effects.

EXAMPLE 2

SYNTHESIS OF OCM

Crotonyl chloride was obtained from Aldrich Chemical, and octadecyl 3-mercaptopropionate (hereinafter "OMP") was obtained from Evans Chemetics (Lexington, Mass.); both were used without further purification. Pyridine was distilled from BaO and stored over 3Å molecular sieves. Tetrahydrofuran (hereinafter "THF") was freshly distilled from sodium/benzophenone. All glassware was dried with a flame before use.

To a 1-liter flask containing 13.5 g (0.129 mol) crotonyl chloride dissolved in approx. 250 mL THF was added dropwise a solution of 35.2 g (0.098 moles) OMP and 7.7 g (0.097 moles) pyridine in approx. 75 mL THF. Addition to the stirred solution was carried out over a period of 10 minutes. A white solid formed immediately and continued to form. After 1 hour of stirring at room temperature, the mixture was filtered. The filtrate was rotavapped by use of a 40° C. bath to yield 35.6 g (88% yield) of a slurry that solidified to a waxy white solid upon chilling. This material was purified by silica gel chromatography. A dry column (3.5 cm×60 cm) of 60 Å silica, 230–400 mesh (Baxter) was poured. Approximately 2.5 g of the solid reaction product was dissolved in a small volume of chloroform. A small amount of silica was added, and the mixture was rotavapped. The silica with the OCM adsorbed was placed at the head of the column. Elution with 3% (v/v) hexanes in methylene chloride was carried out to yield 1.0 g of pure OCM as a crisp, white solid ($R_f$=0.47 in the same solvent). $^1$H NMR (CDCl$_3$) δ 0.90 ppm [t, 3 H, —(CH$_2$)$_{17}$CH$_3$], 1.2–1.3 [s, 30 H, CH$_3$(CH$_2$)$_{15}$—], 1.6 [m, 2 H, —OCH$_2$CH$_2$—], 1.9 [dd, 3 H, CH$_3$CH=CH—], 2.6 [t, 2 H, —CH$_2$C(O)—], 3.18 [t, 2H, —SCH$_2$—], 4.10 [t, 2H —CO$_2$CH$_2$—], 6.09 [m, 1 H, CH$_3$CH=CH—], 6.9 [m, 1H, CH$_3$CH=CH—].

The reaction of OCM with N-acetylcysteamine was carried out at room temperature as follows: 22.0 mg of OCM was dissolved in 0.6 mL of CDCl$_3$ and 5.7μL of N-acetylcysteamine (1 equivalent) was added. The NMR spectrum was recorded and showed that no reaction had occurred. Then a catalytic amount (0.1 equiv) of the base DBN was added, and the NMR spectrum was recorded immediately and again after 5 minutes. By 5 minutes, more than 60% of the OCM had reacted as judged by the diminished integration of the resonances at 6.9 ppm and 6.1 ppm due to the vinyl protons of the crotonyl moiety of OCM. After 27 minutes, NMR showed that complete reaction has occurred. A COSY spectrum confirmed that the expected product, shown earlier herein, had been formed. Nucleophilic attack by the sulfur atom of N-acetylcysteamine, presumably as the thiolate anion, at the β-position of the unsaturated thiol ester generated the expected covalent adduct. NMR characteristics of the product are as follows:

$^1$H NMR (CDCl$_3$) δ 0.85 ppm [t, 3 H, CH$_3$(CH$_2$)$_{17}$—], 1.2–1.3 [m, 30 H, —(CH$_2$)$_{15}$—], 1.24 [dd, 3 H, CH$_3$CH(S—)CH$_2$—], 1.6 [m, 2 H, —CO$_2$CH$_2$CH$_2$—], 2.0 [s, 3 H, cysteamine CH$_3$], 2.6 [m, 2H, —C(O)SCH$_2$CH$_2$—], 2.65 [m, 2H, cysteamine SCH$_2$CH$_2$—], 2.7 [m, 2 H, CH$_3$CH(S—)CH$_2$—], 3.2 [t, 2H, —C(O)SCH$_2$CH$_2$—], 3.3 [q, 1 H, CH$_3$CH(S—)CH$_2$—], 3.45 [m, 2 H, cysteamine —SCH$_2$CH$_2$NH—], 4.1 [t, 3 H, —CO$_2$CH$_2$(CH$_2$)$_{16}$CH$_3$], 6.2 [br s, 1 H, cysteamine NH].

EXAMPLE 3

SYNTHESIS OF DCPEG

DCPEG was synthesized according to the following scheme.

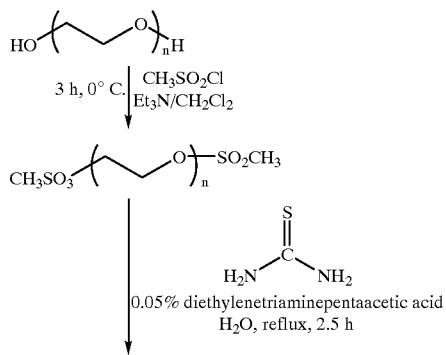

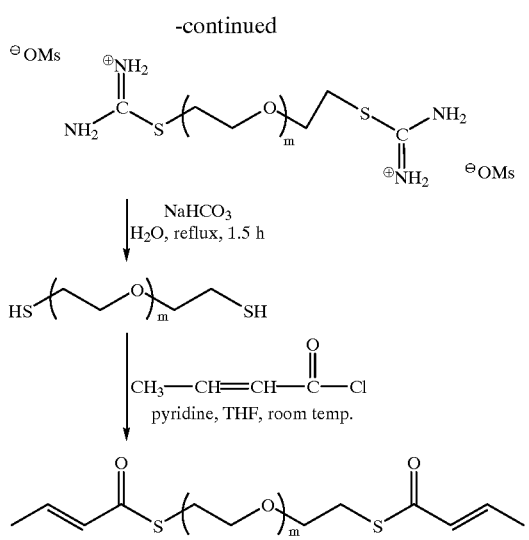

Poly(ethylene glycol) (hereinafter "PEG") with an average molecular weight ($M_n$) of about 400 was obtained from Aldrich and was dried by heating at 70° C. under vacuum for three hours. Triethylamine, methylene chloride and pyridine were purified by distillation. THF was distilled from Na/benzophenone.

Preparation of PEG dimesylate was carried out as follows. PEG (3.65 g, 18 mmol OH-ends) and 3.95 g triethylamine were dissolved in methylene chloride, chilled to 0° C. and then a five-fold excess of methanesulfonyl chloride dissolved in methylene chloride was added dropwise. The solution was stirred at 0° C. for three hours and then it was rotavapped to a syrup, taken up in water and the unreacted methanesulfonyl chloride was destroyed by addition of NaHCO$_3$. The product was then extracted into chloroform, dried with MgSO$_4$ and rotavapped to yield 9.96 g of a light yellow oil (95% yield). $^1$H NMR (CDCl$_3$) δ 3.07 ppm [s, 6 H, CH$_3$SO$_2$—], 3.6 [m, 28 H, —OCH$_2$CH$_2$O—], 3.8 [m, 4 H, —SO$_3$CH$_2$CH$_2$—], 4.4 [m, 4 H, —SO$_3$CH$_2$CH$_2$—].

To prepare the PEG dithiol, 5.0 g of the PEG dimesylate was added to an aqueous solution containing 53.8 mg diethylenetriaminepentaacetic acid and 2.85 g (2 equivalents) of thiourea. The pH was adjusted to 6.7, and the reaction was refluxed for 2.5 hours. The reaction was then cooled and the isothiouronium salt was hydrolyzed by addition of 2.35 g of NaHCO$_3$ (1.5 equivalents) followed by 1.5 hours of reflux. The solution was neutralized with 1 M H$_2$SO$_4$ and the PEG dithiol was extracted into chloroform, dried with MgSO$_4$ and rotavapped to yield 2.18 g of a light amber oil.

Coupling of the PEG dithiol with crotonyl chloride to give DCPEG was carried out as follows. A solution of 2.1 g PEG dithiol (9.0 mmol SH-ends) and 0.656 g (8.3 mmol) pyridine in 10 mL THF was placed in an addition finnel and added dropwise to a stirred solution of 0.857 g (8.5 mmol) crotonyl chloride in 20 mL THF. The solution instantly became cloudy. After 16 hours the reaction was rotavapped to dryness and the residue was taken up in chloroform, washed extensively with aqueous NaHCO$_3$ and dried to give 1.7 g of an amber oil (70% yield). $^1$H NMR (CDCl$_3$) δ 1.88 ppm, [dd, J=7.6, 1.7 Hz, 6 H, 2 CH$_3$—], 2.88 [t, J=6.6 Hz, 4 H, CH$_2$—], 3.15 [t,J=6.6 Hz, 4H, —CH$_2$—], 3.6–3.75 [m, —OCH$_2$CH$_2$O—], 6.14 [m, 2 H, 2 CH$_3$CH=CH—], 6.91 [m, 2 H, 2CH$_3$CH=CH—].

The reaction of DCPEG with N-acetylcysteamine was followed by NMR: 35.6 mg of DCPEG was dissolved in 0.7 mL CDCl$_3$ and the spectrum was recorded before and after addition of N-acetylcysteamine (1 equivalent per crotonyl moiety). Then 0.1 equivalent of DBN was added. The reaction was found to be complete after 5 minutes, as evidenced by the disappearance of the resonances at 6.14 and 6.91 ppm which correspond to the protons on the crotonyl double bond. NMR of the covalent N-acetylcysteamine adduct confirmed that addition to the β-position of the α, β-unsaturated thiol ester had occurred.

The synthesis of DSPEG can be carried out by a procedure analogous to that described for DCPEG above, except that sorboyl chloride is used in place of crotonyl chloride.

CPEG and SPEG can be synthesized by a procedure analogous to that described for DCPEG above, except the amount of methanesulfonyl chloride is reduced from a 5-fold excess to approximately one half equivalent (per OH-ends) to yield a mixture of unmodified PEG, PEG monomesylate and PEG dimesylate. The purified PEG monomesylate can then be treated with diethylenetriaminepentaacetic acid and thiourea, followed by NaHCO$_3$, to yield PEG monothiol. PEG monothiol can be coupled to crotonyl chloride to yield CPEG, or to sorboyl chloride to yield SPEG.

EXAMPLE 4

PREPARATION OF COMPOSITIONS

A suitable cream containing OCM for application to the skin was formulated as follows.

|   | Ingredient | Percent by weight (wt. %) |
|---|---|---|
| A | Water | 67.7 |
|   | Aculyn 33 | 2.5 |
| B | Mineral Oil | 20.0 |
|   | Lanolin | 4.0 |
|   | Petrolatum | 4.0 |
|   | Ethomeen C-25 | 0.7 |
| C | Triethanolamine | 1.1 |

Mixing Procedure:

First, 86 mg of OCM and 287 mg of part B were gently warmed for a few seconds until OCM dissolved. Second, the solution was placed in a 60–70° C. bath for approximately 5 seconds. Then, 702 mg of part A also at 60–70° C. was added to the solution. After addition of 11 mg of part C, the sample was quickly vortex-mixed and chilled to yield a cream. The pH was found to be 8.2, in the range desired for deprotonation of cysteine sulfhydryl groups, tyrosine's —OH group, and protein —NH$_3^+$ groups.

EXAMPLE 5

PREPARATION OF COMPOSITION

A suitable cream for application to the skin is formulated as follows:

|   | Ingredient | Percent by weight (wt. %) |
|---|---|---|
| A | Water | 67.7 |
|   | Aculyn 33 | 2.5 |
| B | Mineral Oil | 20.0 |
|   | Lanolin | 4.0 |

-continued

|   | Ingredient | Percent by weight (wt. %) |
|---|---|---|
|   | Petrolatum | 4.0 |
|   | Ethomeen C-25 | 0.7 |
| C | Triethanolamine | 1.1 |

Mixing procedure:

A suitable quantity of CPEG, DCPEG, SPEG, DSPEG, OSM, OCM, CMC or SMC or some combination thereof is added to part B and the mixture is brought to 60–70° C. After addition of part A, also at 60–70° C., part C is added and the sample is mixed and quickly chilled to yield a cream. The amount of part C is adjusted to produce a pH of approximately 8.2, in the range desired for deprotonation of cysteine sulfhydryl groups, tyrosine hydroxyl groups, and —NH$_3^+$ groups of lysine and the N-terminus of proteins.

All of the references cited herein are incorporated herein in their entirety.

What is claimed is:

1. A skin care compound having a formula selected from the group consisting of

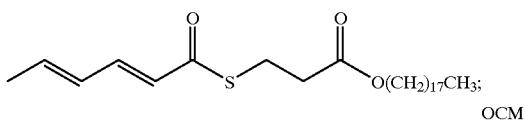

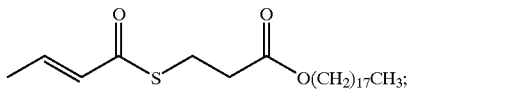

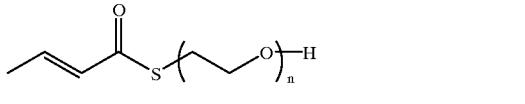

wherein n is primarily 8 to 9;

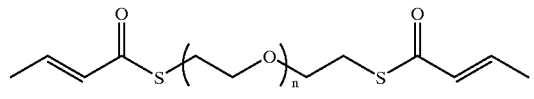

wherein n is primarily 7 to 8;

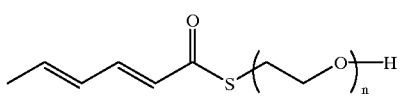

wherein n is primarily 8 to 9;

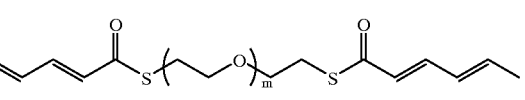

wherein m is primarily 7 to 8;

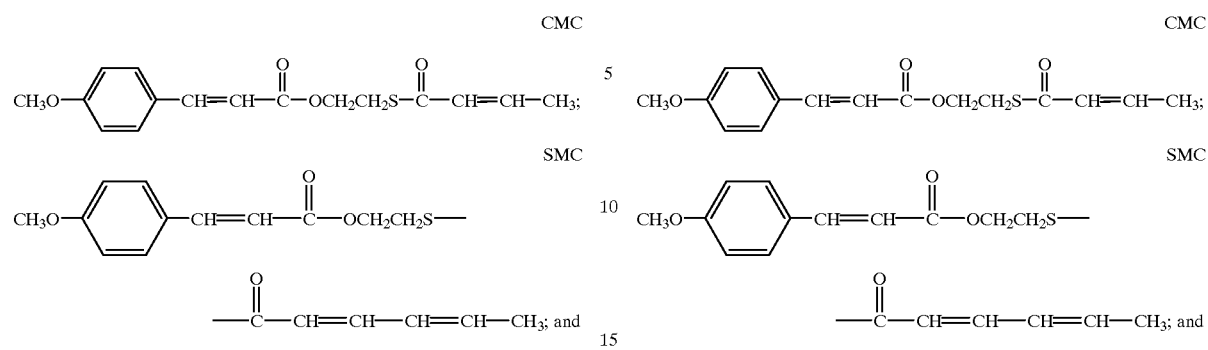

mixtures thereof.

2. A skin care composition comprising a cosmetically acceptable carrier and a compound having a formula selected from the group consisting of

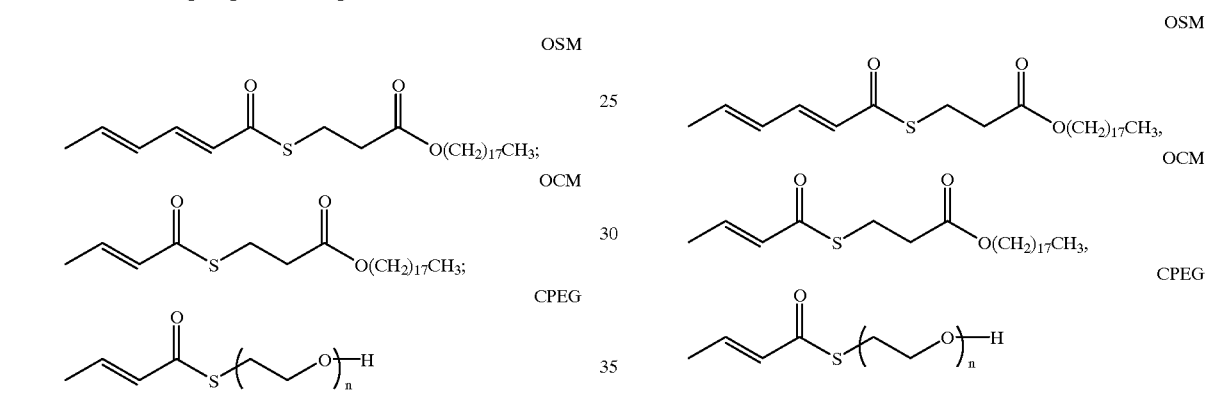

wherein n is primarily 8 to 9;

wherein m is primarily 7 to 8;

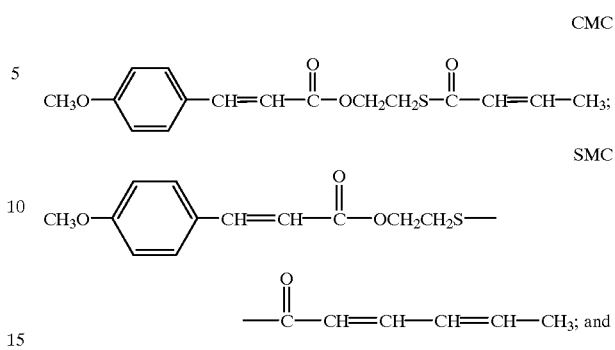

mixtures thereof.

3. A method of conferring a skin care benefit by applying to mammalian skin a compound selected from the group consisting of

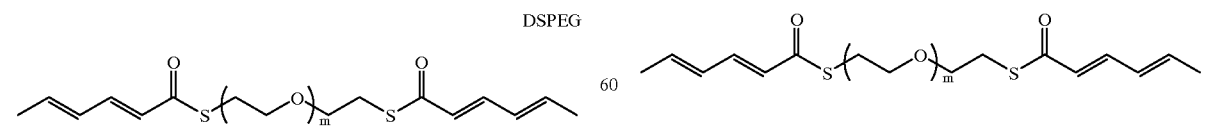

* * * * *